US010098662B2

(12) United States Patent
Boling et al.

(10) Patent No.: US 10,098,662 B2
(45) Date of Patent: Oct. 16, 2018

(54) SURGICAL TOOLS TO FACILITATE DELIVERY OF A NEUROSTIMULATOR INTO THE PTERYGOPALATINE FOSSA

(71) Applicants: Autonomic Technologies, Inc., Redwood City, CA (US); THE CLEVELAND CLINIC FOUNDATION, Cleveland, OH (US)

(72) Inventors: Carl Lance Boling, San Jose, CA (US); Anthony V. Caparso, San Mateo, CA (US); Francis A. Papay, Westlake, OH (US); Ryan Powell, Sunnyvale, CA (US); Jennifer Teng, San Francisco, CA (US); Morgan Clyburn, Menlo Park, CA (US)

(73) Assignees: The Cleveland Clinic Foundation, Cleveland, OH (US); Autonomic Technologies, Inc., Redwood City, CA (US)

( * ) Notice: Subject to any disclaimer, the term of this patent is extended or adjusted under 35 U.S.C. 154(b) by 508 days.

(21) Appl. No.: 14/954,070

(22) Filed: Nov. 30, 2015

(65) Prior Publication Data
US 2016/0081716 A1    Mar. 24, 2016

Related U.S. Application Data

(60) Division of application No. 13/470,480, filed on May 14, 2012, now Pat. No. 9,220,524, which is a
(Continued)

(51) Int. Cl.
*A61N 1/00*  (2006.01)
*A61B 17/34*  (2006.01)
(Continued)

(52) U.S. Cl.
CPC ...... *A61B 17/3468* (2013.01); *A61B 17/0218* (2013.01); *A61B 17/24* (2013.01);
(Continued)

(58) Field of Classification Search
CPC ..... A61B 17/3468; A61B 17/02; A61B 17/24; A61B 17/3211; A61B 2017/320052;
(Continued)

(56) References Cited

U.S. PATENT DOCUMENTS

| 5,558,622 A | 9/1996 | Greenberg |
| 6,093,145 A | 7/2000 | Vom Berg et al. |

(Continued)

FOREIGN PATENT DOCUMENTS

| WO | 2003082123 A2 | 10/2003 |
| WO | 2008066557 A1 | 6/2008 |

OTHER PUBLICATIONS

Theodosopoulos et al., "Endoscopic Approach to the Infratemoral Fossa: Anatomic Study", Neurosurgery 66: 196-203, 2010.
(Continued)

*Primary Examiner* — Lindsey G Wehrheim
(74) *Attorney, Agent, or Firm* — Tarolli, Sundheim, Covell & Tummino LLP

(57) ABSTRACT

A surgical tool configured to facilitate delivery of a neurostimulator to a craniofacial region of a subject includes a handle portion, an elongate shaft having a contoured distal portion, and an insertion groove on the elongate shaft. The elongate shaft is configured to be advanced under a zygomatic bone along a maxillary tuberosity towards a pterygopalatine fossa. The distal portion includes a distal dissecting tip. The insertion groove is configured to receive, support, and guide a medical device or instrument.

11 Claims, 27 Drawing Sheets

Related U.S. Application Data continuation-in-part of application No. 12/688,300, filed on Jan. 15, 2010, now Pat. No. 9,211,133.

(60) Provisional application No. 61/145,122, filed on Jan. 16, 2009.

(51) Int. Cl.

| | | |
|---|---|---|
| *A61B 17/24* | (2006.01) | |
| *A61B 17/3211* | (2006.01) | |
| *A61N 1/05* | (2006.01) | |
| *A61N 1/36* | (2006.01) | |
| *A61N 1/372* | (2006.01) | |
| *A61B 17/02* | (2006.01) | |
| *A61B 17/32* | (2006.01) | |
| *A61N 1/375* | (2006.01) | |

(52) U.S. Cl.
CPC ........ *A61B 17/3211* (2013.01); *A61N 1/0526* (2013.01); *A61N 1/0551* (2013.01); *A61N 1/36075* (2013.01); *A61N 1/37205* (2013.01); *A61B 17/02* (2013.01); *A61B 2017/320052* (2013.01); *A61N 1/0548* (2013.01); *A61N 1/375* (2013.01)

(58) Field of Classification Search
CPC ................. A61B 17/0218; A61N 1/0526; A61N 1/0548; A61N 1/0551; A61N 1/36075; A61N 1/375; A61N 1/37205
See application file for complete search history.

(56) References Cited

U.S. PATENT DOCUMENTS

| | | |
|---|---|---|
| 2003/0236447 A1 | 12/2003 | Ritland |
| 2004/0116977 A1 | 6/2004 | Finch |
| 2005/0059890 A1 | 3/2005 | Deal |
| 2006/0111754 A1 | 5/2006 | Rezai et al. |
| 2006/0195169 A1 | 8/2006 | Gross et al. |
| 2006/0293723 A1 | 12/2006 | Whitehurst et al. |
| 2008/0172102 A1 | 7/2008 | Shalev |
| 2010/0114184 A1 | 5/2010 | Degtyar |
| 2010/0168513 A1* | 7/2010 | Pless .................. A61B 1/00135 600/106 |

OTHER PUBLICATIONS

PCT Int'l. Search Report dated Mar. 30, 2010 for PCT Int'l Appln. No. PCT/US2010/021169, filed Jan. 15, 2010.

* cited by examiner

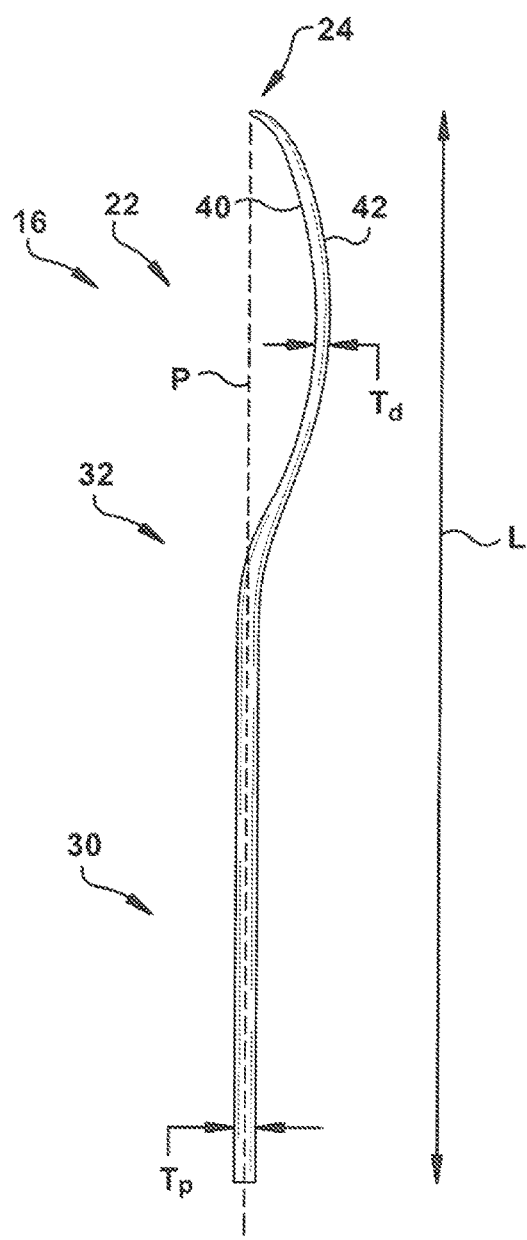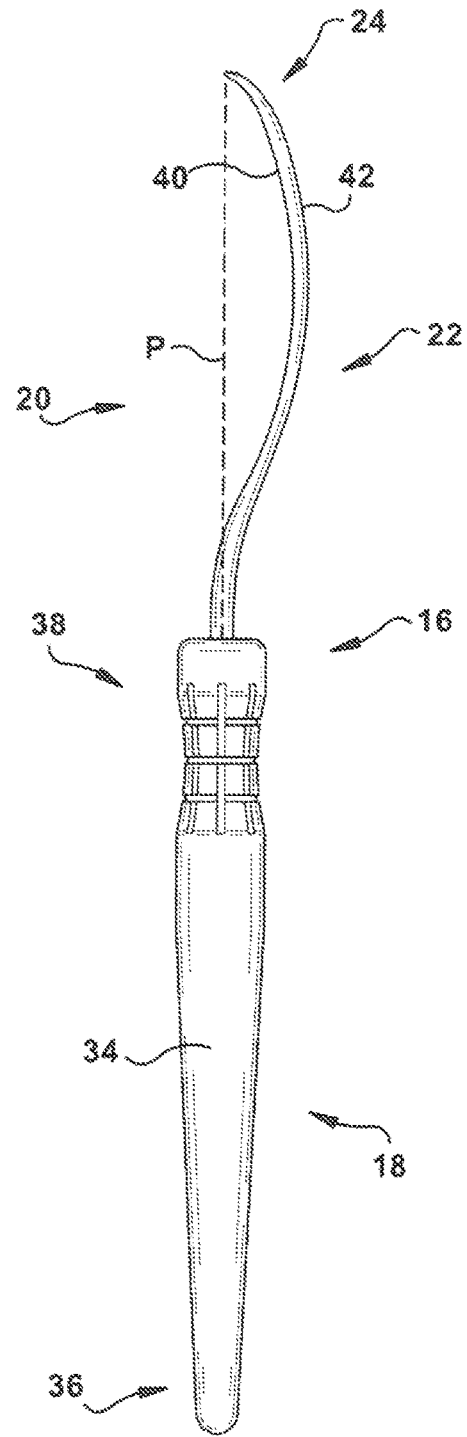
Fig. 4A
Fig. 4B

SURGICAL TOOLS TO FACILITATE DELIVERY OF A NEUROSTIMULATOR INTO THE PTERYGOPALATINE FOSSA

This application is a divisional application of U.S. patent application Ser. No. 13/470,480, filed May 14, 2012, which is a continuation-in-part of U.S. patent application Ser. No. 12/688,300, filed Jan. 15, 2010, which claims priority to U.S. Provisional Patent Application Ser. No. 61/145,122, filed Jan. 16, 2009. This application incorporates the above-identified applications herein by reference in their entirety and claims priority to all aforementioned applications for all purposes.

TECHNICAL FIELD

The present disclosure relates generally to surgical tools configured to facilitate delivery of medical devices to a craniofacial region of a subject, and more particularly to surgical tools configured to facilitate delivery of an implantable neurostimulator to a pterygopalatine fossa of a subject.

BACKGROUND OF THE INVENTION

Electrical stimulation of peripheral and central neural structures has shown increased interest due to the potential benefits it may provide to individuals suffering from many neurological and behavioral diseases. Many of these therapies today are not well accepted due to the invasive nature of the therapy, even though the efficacy is quite good. This has created a need for less invasive therapies that are directed toward patient and physician clinical needs.

Headaches are one of the most debilitating ailments that afflict millions of individuals worldwide. The specific pathophysiology of headaches is unknown. Known sources of headache pain consist of trauma, vascular, autoimmune, degenerative, infectious, drug and medication-induced, inflammatory, neoplastic, metabolic-endocrine, iatrogenic, musculoskeletal and myofacial causes. Also, even though the possible underlying cause of the headache pain is identified and treated, the headache pain may persist.

Currently, the sphenopalatine (pterygopalatine) ganglion (SPG) is a target of manipulation in clinical medicine to treat headaches. The SPG is an extracranial neuronal center located behind the nose. It consists of parasympathetic neurons that innervate (in part) the middle cerebral and anterior cerebral blood vessels, the facial blood vessels, and the lacrimal glands. The SPG also consists of sympathetic and sensory nerve fibers that pass through the SPG in route to their end organs. Manipulation of the SPG is mostly performed in attempted treatments of severe headaches, such as cluster headaches or chronic migraines.

Various clinical approaches have been used for over 100 years to modulate the function of the SPG to treat headaches. These procedures vary from least invasive (e.g., transnasal anesthetic blocks) to much more invasive (e.g., surgical ganglionectomy), as well as procedures, such as surgical anesthetic injections, ablations, gamma knife and cryogenic surgery. These later procedures are very invasive, and most are non-reversible. In both cases, the surgical approach is typically through the nostrils or the greater palatine foramen.

SUMMARY OF THE INVENTION

According to another aspect of the present disclosure, a surgical tool configured to provide surgical access to a craniofacial region of a subject includes a handle portion, an elongate shaft having a contoured distal portion, and an insertion groove on the elongate shaft. The distal portion is shaped and configured to maintain contact with a posterior maxilla and elevate a periosteum off of the posterior maxilla to avoid soft tissue dissection. The distal portion includes a distal dissecting tip. The insertion groove is configured to receive a tunneling member.

According to another aspect of the present disclosure, a surgical tool configured to deliver a neurostimulator to a craniofacial region of a subject includes a handle portion, an elongate shaft having a contoured distal portion, and an insertion groove on the elongate shaft. The elongate shaft is configured to be advanced under a zygomatic bone along a maxillary tuberosity towards a PPF. The distal portion includes a distal dissecting tip. The insertion groove is configured to deploy the neurostimulator.

According to another aspect of the present disclosure, a method is provided for delivering a neurostimulator to within close proximity of a sphenopalatine ganglion (SPG). One step of the method includes making an incision at a gingival-buccal insertion site. A first surgical tool is then inserted into the incision. Next, the first surgical tool is advanced under a zygomatic bone along a maxillary tuberosity towards PPF to form a first surgical access cavity. A second surgical access cavity is then formed at an end of the first surgical access site that is in close proximity to the SPG. The neurostimulator is delivered in close proximity to the SPG via the first and second surgical access cavities.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 4A is a side view of the surgical tool in FIGS. 2A-B (handle omitted for clarity);

FIG. 4B is a side view of the surgical tool in FIG. 4A with a handle;

DETAILED DESCRIPTION

Figure 1:
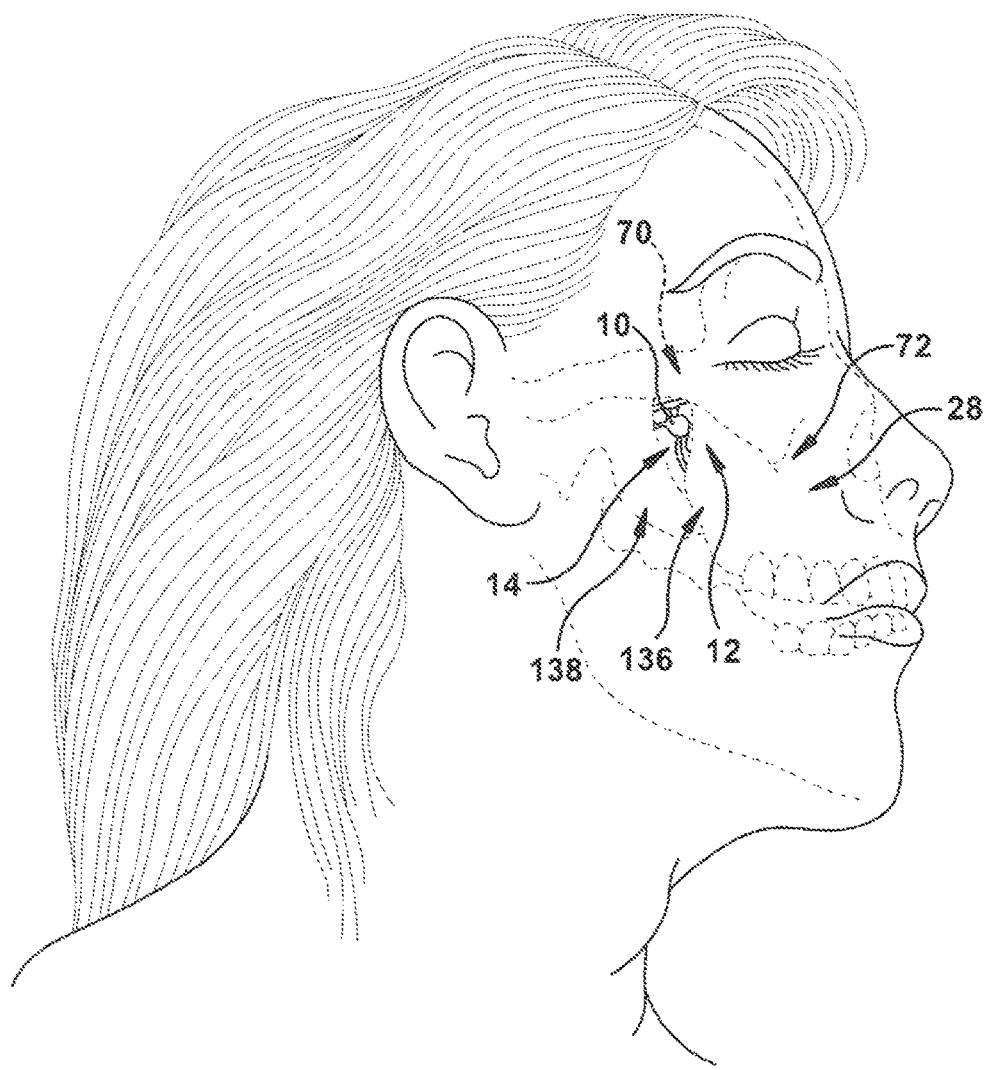
FIG. 1 is a perspective view showing part of the nervous innervation of the anterior craniofacial skeleton.

The present disclosure relates generally to surgical tools configured to facilitate delivery of medical devices to a craniofacial region of a subject, and more particularly to surgical tools configured to facilitate delivery of an implantable neurostimulator to a pterygopalatine fossa (PPF) of a subject. Surgical tools of the present disclosure generally comprise a handle portion, an elongate shaft that includes a distal dissecting tip and is configured to be advanced under a zygomatic bone along a maxillary tuberosity towards a PPF, and an insertion groove on the elongated shaft that is configured to receive, support, and guide a medical device or instrument. As discussed in greater detail below, the present disclosure may be employed to assist in treating a variety of chronic or acute medical conditions. Examples of such medical conditions can include, but are not limited to, pain (e.g., headache and/or facial pain), movement disorders, epilepsy, cerebrovascular diseases, autoimmune diseases, sleep disorders, autonomic disorders, neurological disorders, urinary bladder disorders, abnormal metabolic states, disorders of the muscular system, and neuropsychiatric disorders.

Unless otherwise defined, all technical terms used herein have the same meaning as commonly understood by one of ordinary skill in the art to which the present disclosure pertains.

In the context of the present disclosure, the term "headache" can refer to migraines, tension headaches, cluster headaches, trigeminal neuralgia, secondary headaches, tension-type headaches, chronic and epsiodic headaches, medication overuse/rebound headaches, chronic paroxysmal hemicrinia headaches, hemicranias continua headaches, post-traumatic headaches, post-herpetic headaches, vascular headaches, reflex sympathetic dystrophy-related headaches, cervicalgia headaches, caroidynia headaches, sciatica headaches, trigeminal headaches, occipital headaches, maxillary headaches, chary headaches, paratrigeminal headaches, petrosal headaches, Sluder's headache, vidian headaches, low cerebrospinal fluid pressure headaches, temporomandibular joint (TMJ) headaches, causalgia headaches, myofascial headaches, all primary headaches (e.g., primary stabbing headache, primary cough headache, primary exertional headache, primary headache associated with sexual activity, hypnic headache, and new daily persistent headache), all trigeminal autonomic cephalagias (e.g., episodic paroxysmal hemicranias, short-lasting unilateral neuralgiform headache attacks with conjunctival injection and tearing (SUNCT) and short-lasting unilateral neuralgiform headache attacks with cranial autonomic symptoms (SUNA)), chronic daily headaches, occipital neuralgia, atypical facial pain, neuropathic trigeminal pain, and miscellaneous-type headaches.

As used herein, the term "cluster headache" can refer to extremely painful and debilitating headaches that occur in groups or clusters. Cluster headaches can include chronic or episodic cluster headaches, cluster-type headaches, histamine headaches, histamine cephalalgia, Raedar's syndrome and sphenopalatine neuralgia.

As used herein, the term "migraine" can refer to an intense and disabling chronic or episodic headache typically characterized by severe pain in one or both sides of the head. Migraines can include, but are not limited to, migraine without aura, migraine with aura, migraine with aura but without headache, menstrual migraines, variant migraines, transformed migraines, menstrual migraines, complicated migraines, hemiplegic migraines, atypical migraines, chronic migraines, basilar-type migraines, childhood periodic syndromes that are commonly precursors of migraine (e.g., abdominal, cyclic vomiting, BPV, etc.), status migrainous, and all types of probable migraines.

As used herein, the term "facial pain" can refer to direct pain that typically involves nerves supplying the face or, alternatively, indirect (referred) pain from other structures in the head, e.g., blood vessels. The pain may be related to headache (e.g., migraine), muscular syndromes (e.g., TMJ), and herpetic or rheumatic disease or injury.

As used herein, the terms "modulate" or "modulating" can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, biological, magnetic, optical or chemical, or a combination of two or more of these. The terms can also be used to refer to a masking, altering, overriding, or restoring of neuronal activity.

As used herein, the term "subject" can refer to any warm-blooded organism including, but not limited to, human beings, pigs, rats, mice, dogs, goats, sheep, horses, monkeys, apes, rabbits, cattle, etc.

As used herein, the term "prevent" shall have its plain and ordinary meaning to one skilled in the art of pharmaceutical or medical sciences. For example, "prevent" can mean to stop or hinder a medical condition, such as a headache.

As used herein, the terms "treat" or "treating" shall have their plain and ordinary meaning to one skilled in the art of pharmaceutical or medical sciences. For example, "treat" or "treating" can mean to prevent or reduce a medical condition, such as a headache.

As used herein, the term "medical condition" can refer to pain, movement disorders, epilepsy, cerebrovascular diseases, autoimmune diseases, sleep disorders, autonomic disorders, urinary bladder disorders, abnormal metabolic states, disorders of the muscular system, infectious and parasitic diseases (as provided in ICD-9 codes 1-139), neoplasms (as provided in ICD-9 codes 140-239), endocrine diseases, nutritional and metabolic diseases, immunological diseases (as provided in ICD-9 codes 240-279), diseases of the blood and blood-forming organs (as provided in ICD-9 codes 280-289), mental disorders (as provided in ICD-9 codes 290-319), diseases of the nervous system (as provided in ICD-9 codes 320-359), diseases of the sense organs (as provided in ICD-9 codes 360-389), diseases of the circulatory system (as provided in ICD-9 codes 390-459), diseases of the respiratory system (as provided in ICD-9 codes 460-519), diseases of the digestive system (as provided in ICD-9 codes 520-579), diseases of the genitourinary system (as provided in ICD-9 codes 580-629), diseases of the skin and subcutaneous tissue (as provided in ICD-9 codes 680-709), diseases of the musculoskeletal system and connective tissue (as provided in ICD-9 codes 710-739), congenital anomalies (as provided in ICD-9 codes 740-759), certain conditions originating in the perinatal period (as provided in ICD-9 codes 760-779), and symptoms, signs, and ill-defined conditions (as provided in ICD-9 codes 780-799).

Pain treatable by the present disclosure can be caused by conditions including, but not limited to, migraine headaches, including migraine headaches with aura, migraine headaches without aura, menstrual migraines, migraine variants, atypical migraines, complicated migraines, hemiplegic migraines, transformed migraines, and chronic daily migraines, episodic tension headaches, chronic tension headaches, analgesic rebound headaches, episodic cluster headaches, chronic cluster headaches, cluster variants, chronic paroxysmal hemicranias, hemicrania continua, post-traumatic headache, post-traumatic neck pain, post-herpetic neuralgia involving the head or face, pain from spine fracture secondary to osteoporosis, arthritis pain in the spine, headache related to cerebrovascular disease and stroke, headache due to a vascular disorder, reflex sympathetic dystrophy, cervicalgia (which may be due to various causes including, but not limited to, muscular, discogenic or degenerative, including arthritic, posturally related or metastatic), glossodynia, carotidynia, cricoidynia, otalgia due to middle ear lesion, gastric pain, sciatica, maxillary neuralgia, laryngeal pain, myalgia of neck muscles, trigeminal neuralgia (sometimes also termed tic douloureux), post-lumbar puncture headache, low cerebro-spinal fluid pressure headache, TMJ joint disorder, atypical facial pain, ciliary neuralgia, paratrigeminal neuralgia (sometimes also termed Raeder's syndrome), petrosal neuralgia, Eagle's syndrome, idiopathic intracranial hypertension, orofacial pain, myofascial pain syndrome involving the head, neck and shoulder, chronic migraneous neuralgia, cervical headache, paratrigeminal paralysis, sphenopalatine ganglion (SPG) neuralgia (sometimes also termed lower-half headache, lower facial neuralgia syndrome, Sluder's neuralgia and Sluder's syndrome), carotidynia, vidian neuralgia, causalgia, atypical odontalgia, cluster tic syndrome, geniculate neuralgia, glossopharyngeal neuralgia, occipital neuralgia, temporal arteritis, and/or a combination of the above.

Movement disorders treatable by the present disclosure may be caused by conditions including, but not limited to, Parkinson's disease, cerebropalsy, dystonia, essential tremor and hemifacial spasms.

Epilepsy treatable by the present disclosure may be, for example, generalized or partial.

Cerebrovascular disease treatable by the present disclosure may be caused by conditions including, but not limited to, aneurysms, strokes, and cerebral hemorrhage.

Autoimmune diseases treatable by the present disclosure include, but are not limited to, multiple sclerosis.

Sleep disorders treatable by the present disclosure may be caused by conditions including, but not limited to, circadian rhythm disorders, sleep apnea and parasomnias.

Autonomic disorders treatable by the present disclosure may be caused by conditions including, but not limited to, gastrointestinal disorders, including but not limited to gastrointestinal motility disorders, nausea, vomiting, diarrhea, chronic hiccups, gastroesophageal reflux disease, and hypersecretion of gastric acid, autonomic insufficiency, autonomic instability, excessive epiphoresis, excessive rhinorrhea, and cardiovascular disorders including, but not limited, to cardiac dysrythmias and arrythmias, hypertension, carotid sinus disease, Holmes-Adie syndrome, orthostatic hypotension, striatonigral degeneration, vasovagal syncope, Lyme disease and autonomic instability.

Neurological disorders treatable by the present disclosure may be caused by conditions including, but not limited to, hemifacial spasm, Melkersson-Rosenthal syndrome, and Parry-Romberg syndrome.

Urinary bladder disorders treatable by the present disclosure may be caused by conditions including, but not limited to, spastic or flaccid bladder.

Abnormal metabolic states treatable by the present disclosure may be caused by conditions including, but not limited to, hyperthyroidism or hypothyroidism.

Disorders of the muscular system treatable by the present disclosure can include, but are not limited to, muscular dystrophy, and spasms of the upper respiratory tract and face.

Neuropsychiatric or mental disorders treatable by the present disclosure may be caused by conditions including, but not limited to, depression, schizophrenia, bipolar disorder, and obsessive-compulsive disorder.

A brief discussion of the pertinent anatomy and neurophysiology is provided to assist the reader with understanding the present disclosure. The autonomic nervous system innervates numerous pathways within the human body and consists of two divisions: the sympathetic and the parasympathetic nervous systems. The sympathetic and parasympathetic nervous systems are antagonistic in their action, balancing the other system's effects within the body. The sympathetic nervous system (SNS) usually initiates activity within the body, preparing the body for action, while the parasympathetic nervous system (PNS) primarily counteracts the effects of the SNS.

The sphenopalatine ganglia 10 are located on both sides of the head (FIG. 1). It shall be assumed for the following discussion of the present disclosure that reference is being made to the SPG 10 located on the left side of the head. The SPG 10 is located behind the posterior maxilla 12 in the PPF 14, posterior to the middle nasal turbinate (not shown in detail). The SPG 10 is part of the parasympathetic division of the autonomic nervous system; however, the SPG has both sympathetic and parasympathetic nerve fibers, as well as sensory and motor nerve fibers either synapsing within the ganglion (e.g., parasympathetic) or fibers that are passing through the ganglion and not synapsing (e.g., sympathetic, sensory and motor).

The parasympathetic activity of the SPG 10 is mediated through the greater petrosal nerve (not shown), while the sympathetic activity of the SPG is mediated through the deep petrosal nerve (not shown), which is essentially an extension of the cervical sympathetic chain (not shown). Sensory sensations generated by or transmitted through the SPG 10 include, but are not limited to, sensations to the upper teeth, feelings of foreign bodies in the throat, and persistent itching of the ear. The SPG 10 transmits sensory information, including pain, to the trigeminal system via the maxillary division and ophthalmic division (not shown).

One aspect of the present disclosure includes a surgical tool 16 (FIGS. 2A-B) configured to provide surgical access to a craniofacial region of a subject. The surgical tool 16 comprises a handle portion 18, an elongate shaft 20 that includes a contoured distal portion 22 having a flared distal dissecting tip 24, and an insertion groove 26 on the elongate shaft. The surgical tool 16 (FIG. 3) is designed and configured to be inserted trans-orally from an incision located on the anterior maxilla 28. Advantageously, the distal portion 22 of the elongate shaft 20 is shaped and configured to maintain contact with a posterior maxilla 12 and elevate a periosteum off of the posterior maxilla to avoid soft tissue dissection. Consequently, the contoured design of the distal portion 22 can prevent unwanted soft tissue injury or bleeding during use of the surgical tool 16.

As shown in FIG. 4A, the surgical tool 16 comprises a proximal portion 30, a contoured distal portion 22, and an intermediate portion 32 extending between the proximal portion and the distal portion. The proximal portion 30 and the intermediate portion 32 define a longitudinal plane P that extends between the proximal and intermediate portions. The surgical tool 16 can have a length L of about 10 cm to about 30 cm. For example, the surgical tool 16 can have a length L of about 12 cm (e.g., 12.4 cm). The surgical tool 16 can be made of a rigid or semi-rigid medical grade metal or metal alloy, such as titanium or stainless steel, medical grade plastics (e.g., PEEK, polycarbonate, nylon), ceramics (e.g., aluminum, zirconium oxide), glass, combinations of metals, ceramics, plastics or plastic composites, and the like.

The proximal portion 30 of the surgical tool 16 can have a thickness $T_p$ of about 0.5 mm to about 8 mm, such as about 2 mm to about 4 mm (e.g., about 3 mm). The intermediate portion 32 can have a thickness that is similar or identical to the thickness $T_p$ of the proximal portion 30. It will be appreciated, however, that the thickness of the intermediate portion 32 can decrease as the intermediate portion tapers to the distal portion 22. As shown in FIG. 4B, the proximal portion 30 includes an ergonomic handle 34 that collectively forms the handle portion 18 and is securely disposed thereon. The handle 34 can have a length of about 6 cm to about 12 cm, and vary in diameter from a proximal end 36 (e.g., about 0.5 cm to about 3 cm) to a distal end 8 (e.g., about 0.5 cm to about 2 cm). The handle 34 can include various features to provide grip and tactile maneuverability, such as circumferential ridges or a cross-hatched precut pattern into the material forming the handle. The handle 34 can be made of a rigid or semi-rigid medical grade metal or metal alloy, such as stainless steel, medical grade plastics, polymers, and the like.

Figure 5:
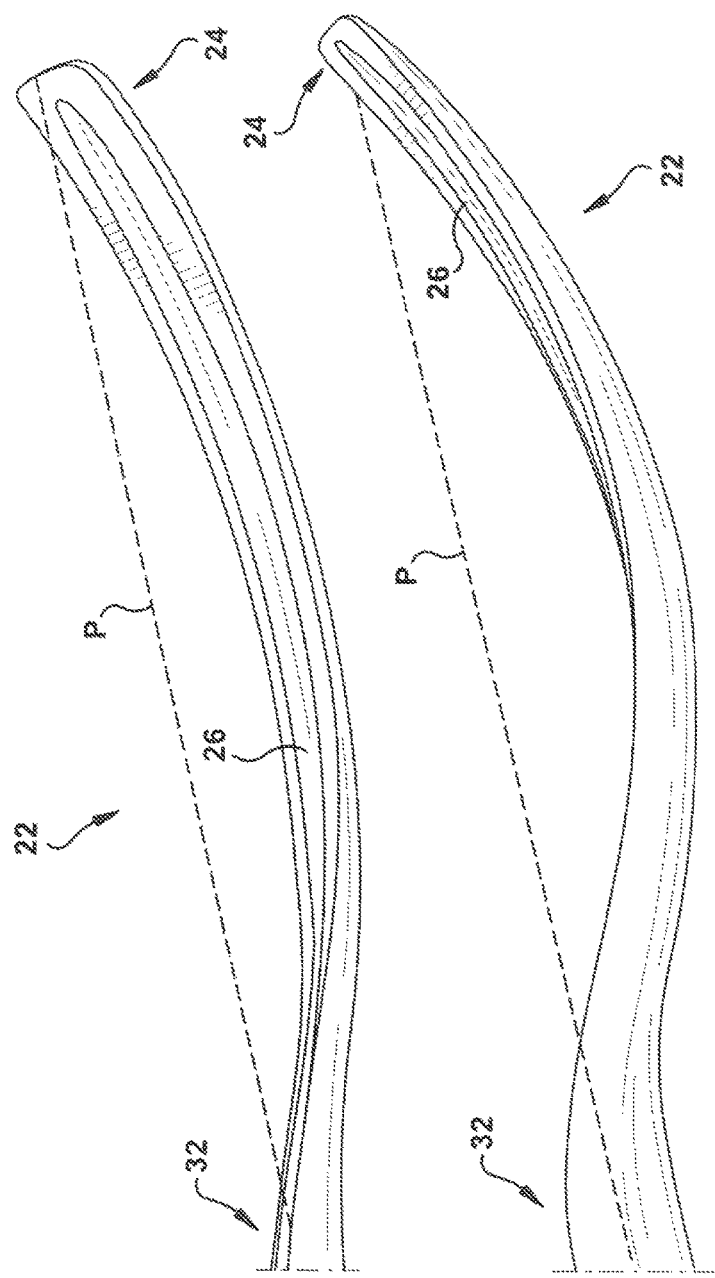
FIG. 5 is an image showing an alternative configuration of the distal portion in FIGS. 2A-B.

The distal portion 22 of the surgical tool 16 is shaped and configured to allow a user to simply and accurately traverse the anterior craniofacial skeletal anatomy to reach the PPF 14. The distal portion 22 is defined by oppositely disposed first and second major surfaces 40 and 42, which collectively form an arcuate shape relative to the longitudinal plane P. For example, the first major surface 40 of the distal portion 22 has a concave shape relative to the longitudinal plane P. An alternative configuration of the surgical tool 16 is shown in FIG. 5. In FIG. 5, the first major surface 40 can be vertically offset relative to the longitudinal plane P (e.g., by about 10° to about 90° so that the distal portion 22 has a partly twisted or helical configuration.

The distal portion 22 (FIGS. 4A-B) can have a thickness $T_d$ of about 2 mm to about 5 mm. The thickness $T_d$ of the distal portion 22 can be uniform or, alternatively, the thickness $T_d$ can decrease or taper at the distal dissecting tip 24. The distal portion 22 can have a radius of curvature so that a user can maintain contact with the posterior maxilla 12 while advancing the surgical tool 16 to the PPF 14. For example, the distal portion 22 can have a radius of curvature of about 8 cm to about 3 cm. Additionally, at least a portion of the distal dissecting tip 24 can be collinear with the longitudinal plane P.

Figures 2A, 2B:
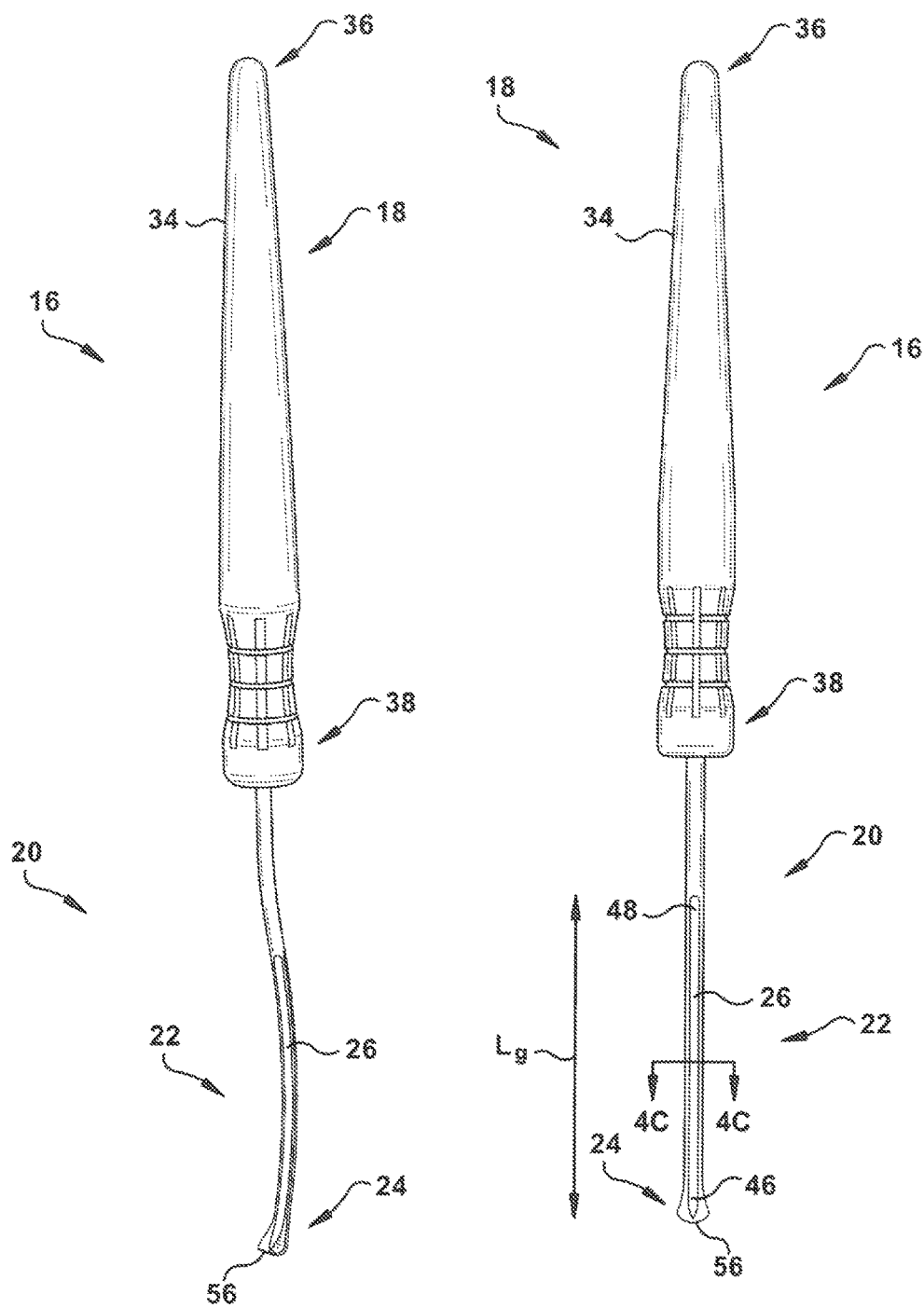
FIG. 2A is a perspective view of a surgical tool configured to provide surgical access to a craniofacial region of a subject constructed in accordance with one aspect of the present disclosure.
FIG. 2B is a top view of the surgical tool in FIG. 2A.
Figure 3:
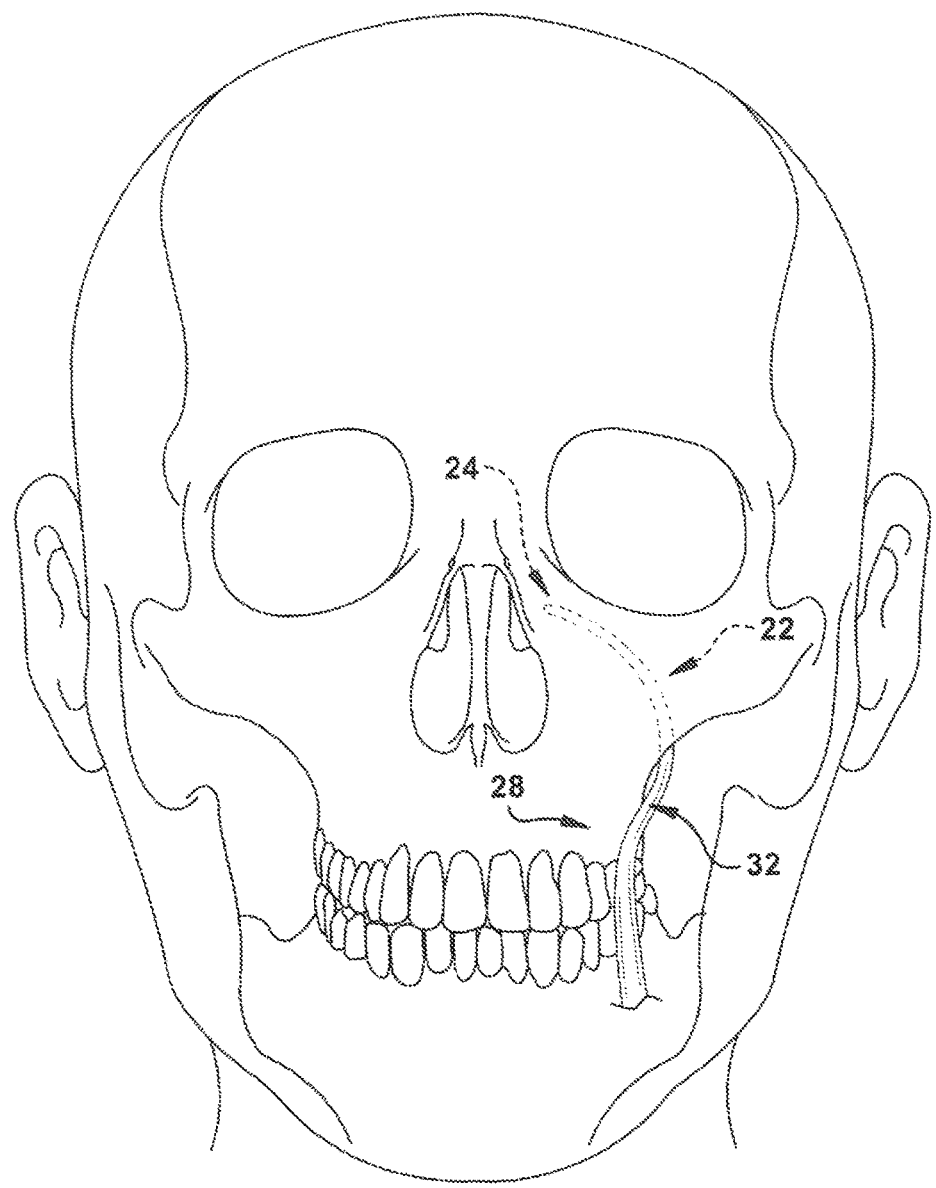
FIG. 3 is a schematic illustration showing a distal portion of the surgical tool in FIGS. 2A-B inserted into a craniofacial region of a subject.

The surgical tool 16 (FIGS. 2A-B) additionally includes an insertion groove 26 on the elongate shaft 20 and, in particular, on the distal portion 22. The insertion groove 26 is adapted, shaped, and configured to receive, support, and guide a tunneling member 44 (FIG. 22), such an electrode lead blank. The tunneling member 44 (e.g., an electrode lead blank) can include any device that has approximately the same diameter of an electrode lead and is configured as a blunt dissector to create a path for the electrode lead. As shown in FIGS. 2A-B, the insertion groove 26 extends across the distal portion 22 of the surgical tool 16 between the distal dissecting tip 24 and the intermediate portion 32. For example, the insertion groove 26 can extend across only the distal portion 22 of the surgical tool 16 and not the intermediate portion 32 and/or the proximal portion 30.

Figure 4C:
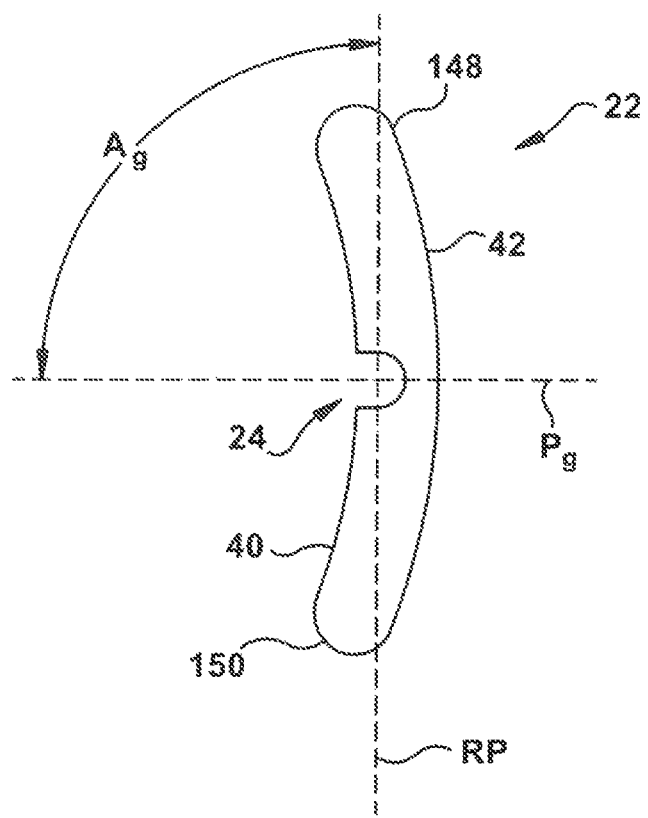
FIG. 4C is a cross-sectional view taken along Line 4C-4C in FIG. 2B.
Figure 6A:
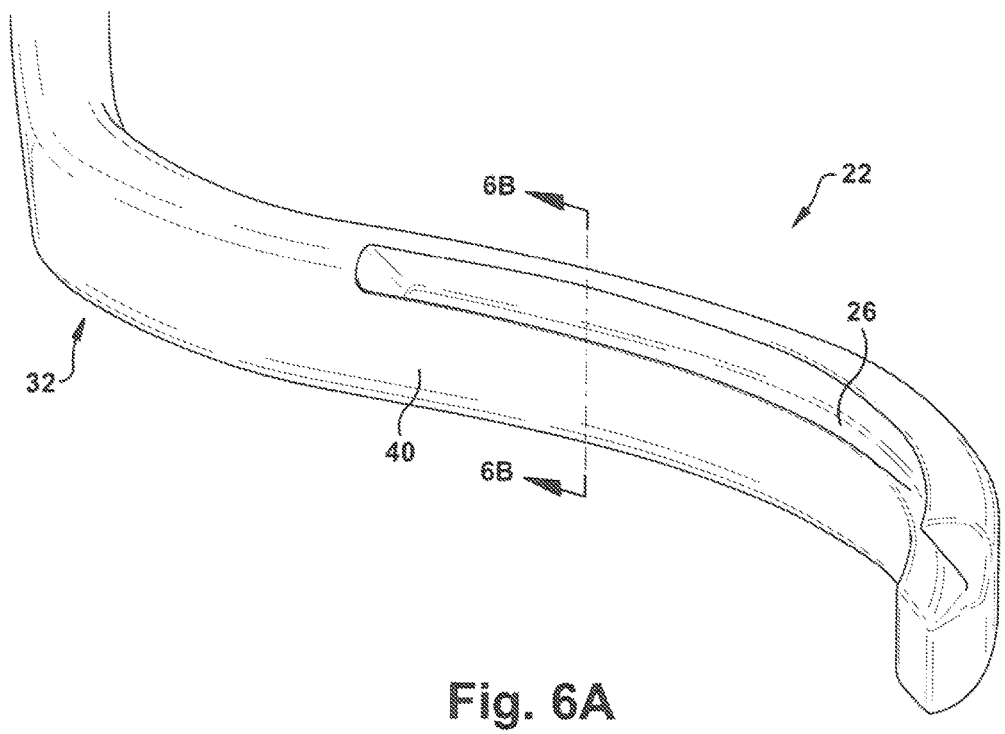
FIG. 6A is a perspective view showing an alternative configuration of the insertion groove in FIGS. 2A-B.
Figure 6B:
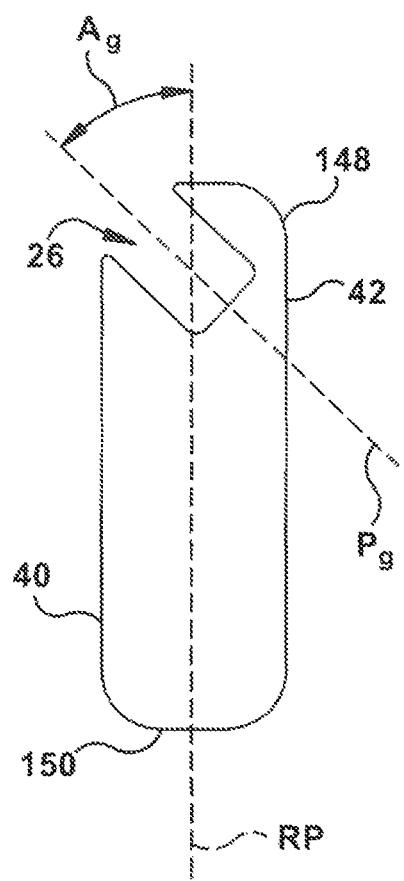
FIG. 6B is a cross-sectional view taken along Line 6B-6B in FIG. 6A.
Figure 7A:
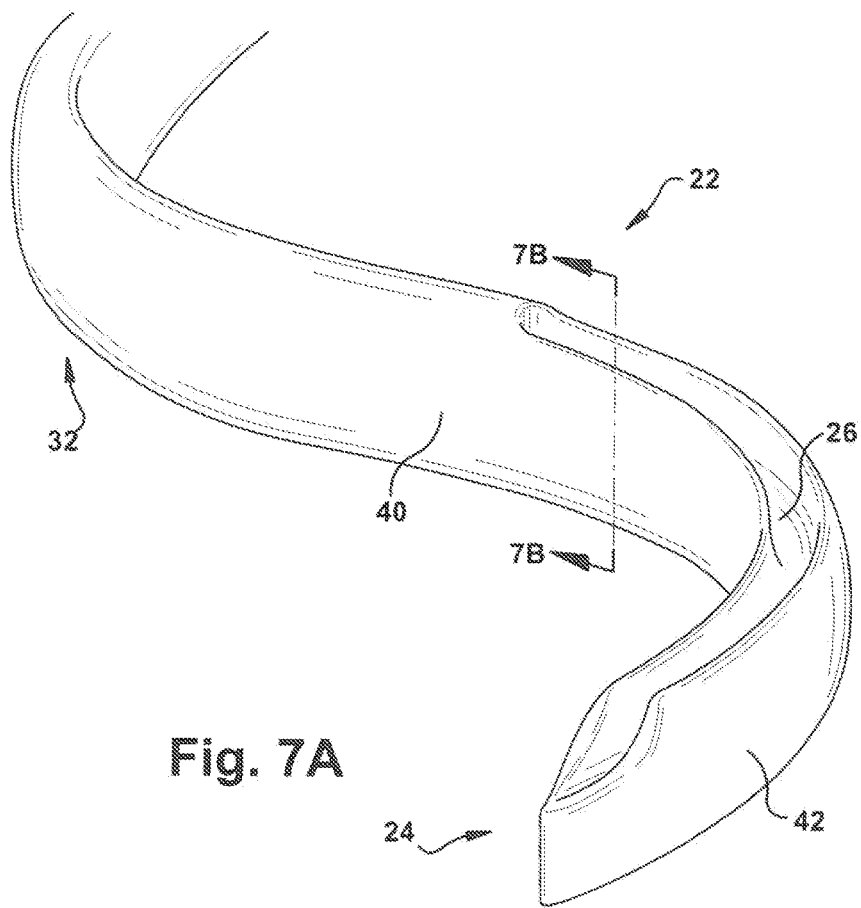
FIG. 7A is a perspective view showing another alternative configuration of the insertion groove in FIGS. 2A-B.
Figure 7B:
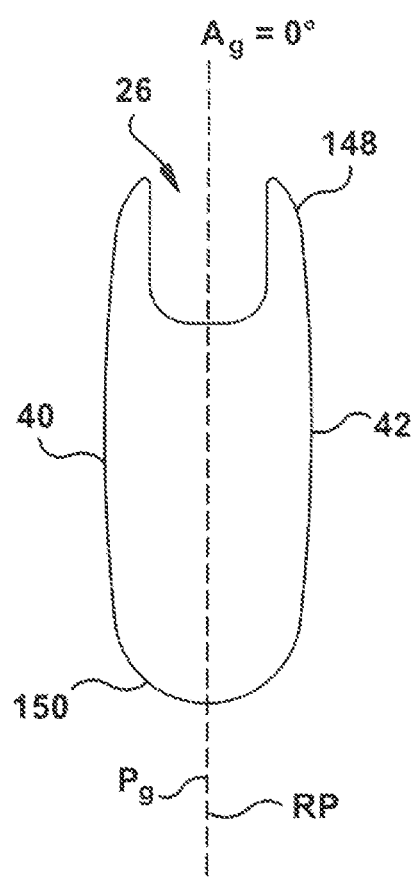
FIG. 7B is a cross-sectional view taken along Line 7B-7B in FIG. 7A.

The insertion groove 26 can be embedded or recessed in the first major surface 40 of the distal portion 22. The insertion groove 26 is recessed in the first major surface at angle $A_g$. The angle $A_g$ is formed between a radial plane RP that extends between opposing edges 148 and 150 of the distal portion 22, and a plane $P_g$ that extends transverse to the length $L_g$ of the insertion groove 26. As shown in FIG. 4C, the angle $A_g$ can be about 90°. Alternatively, the angle $A_g$ can be about 45° (FIGS. 6A-B). In another example, the angle $A_g$ can be less than about 10° (e.g., 0°) where the insertion groove 26 extends along an opposing edge 148 of the distal portion 22 (FIGS. 7A-B). It will be appreciated that the configurations of the surgical tool 16 shown in FIGS. 6A-B and FIGS. 7A-B may or may not include a flared distal dissecting tip 24 (as described below).

Figure 22:
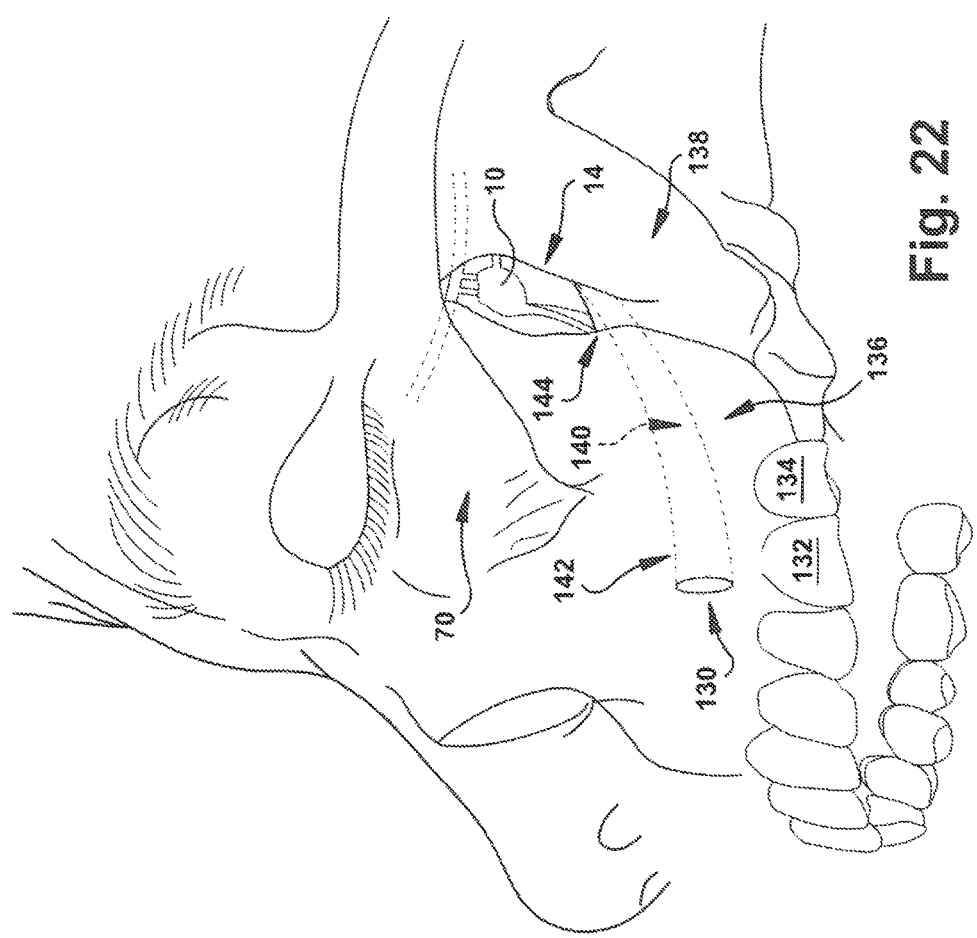
FIG. 22 is a perspective view showing a surgical access cavity formed by the surgical tool in FIG. 21.

The particular dimensions of the insertion groove 26 can vary depending upon the dimensions of surgical guide 16 and/or the dimensions of the tunneling member 44 (FIG. 22). In one example of the present disclosure, all or only a portion of the insertion groove 26 can have a depth of between about 0.5 mm and about 1.2 mm, a width $W_g$ (FIG. 8) of between about 1 mm and about 2 mm (e.g., 1.6 mm), and a length $L_g$ (FIG. 2B) of between about 2 cm and about 8 cm (e.g., 6 cm). The insertion groove 26 can have a semi-circular cross-sectional shape, for example, or any other cross-sectional shape (e.g., square-shaped, V-shaped, etc.) to facilitate engagement of the surgical tool 16 with the tunneling member 44.

Figure 8:
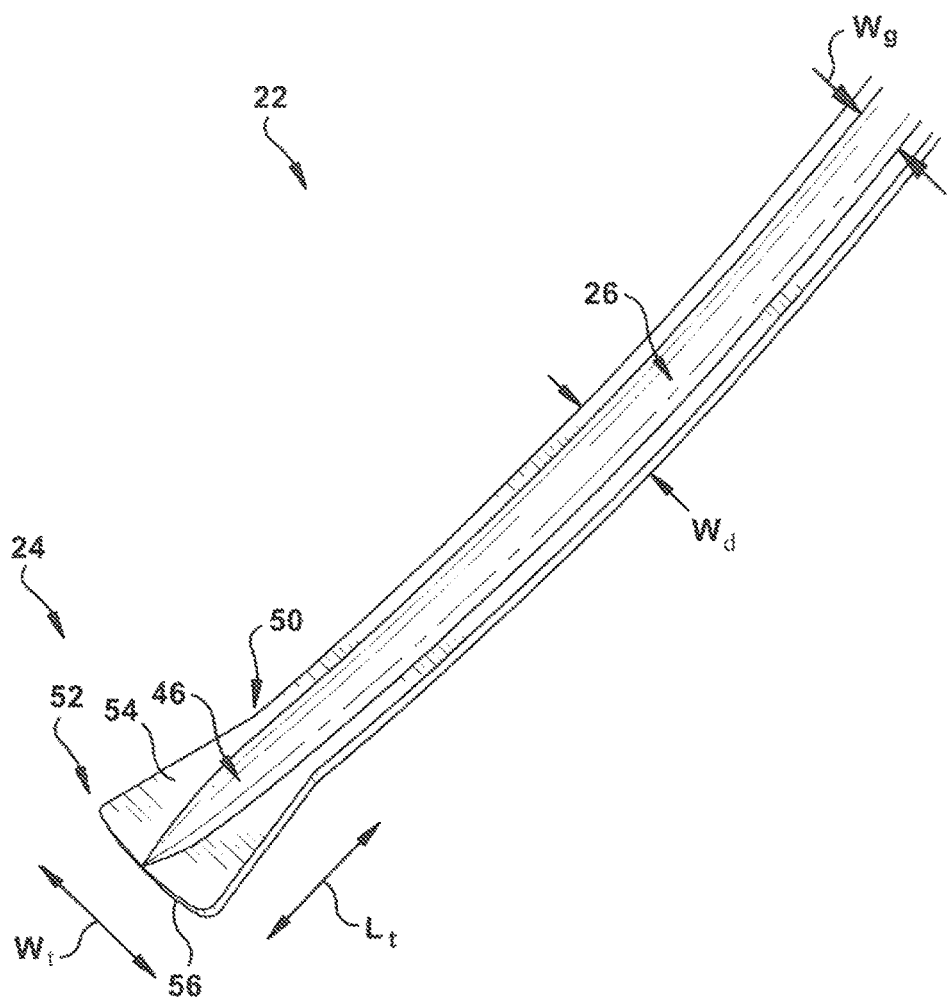
FIG. 8 is a magnified perspective view showing the distal portion of the surgical tool in FIGS. 2A-B.

The depth and width $W_g$ of the insertion groove 26 can vary across the length $L_g$ of the insertion groove to facilitate engagement and release of the tunneling member 44 from the surgical tool 16. For example, the depth of the insertion groove 26 tapers from a distal end 46 of the insertion groove to a proximal end 48 of the insertion groove. More particularly, the proximal end 48 of the insertion groove 26 includes a first depth that is greater than a second depth at the distal end 46 of the insertion groove. As shown in FIG. 8, the depth of the insertion groove 26 at a proximal end 50 of the distal dissecting tip 24 gradually decreases towards a distal end 52 of the distal dissecting tip until the insertion groove becomes flush with a first surface 54 of the distal dissecting tip.

The width $W_g$ of the insertion groove 26 also tapers from the proximal end 48 to the distal end 46. As shown in FIG. 8, the width $W_g$ of the insertion groove 26 at the proximal end 50 of the distal dissecting tip 24 gradually decreases towards the distal end 52 of the distal dissecting tip until the insertion groove becomes flush with the first surface 54 of the distal dissecting tip. The varying depth and width $W_g$ of the insertion groove 26 facilitates engagement and accurate control of the tunneling member 44 during operation of the surgical tool 16.

The distal portion 22 of the surgical tool 16 can include a flared distal dissecting tip 24. By "flared" it is meant that all or only a portion of the distal dissecting tip 24 is shaped and configured to extend away from the distal portion 22 of the elongated shaft 20 axially and/or distally, and typically also radially. The distal dissecting tip 24 includes a length $L_t$ that extends between a proximal end 50 and a distal end 52 thereof. The length $L_t$ can be about 0.1 cm to about 1 cm, such as about 0.1 cm to about 0.5 cm (e.g., 0.25 cm). The distal dissecting tip 24 also includes a width $W_t$ that increases from the proximal end 50 to the distal end 52 of the tip. The width $W_t$ of the distal dissecting tip 24 is greater than the width $W_d$ of the distal portion 22. In one example of the present disclosure, the width $W_t$ at the distal end 52 of the distal dissecting tip 24 can be about 2.5 mm to about 6 mm (e.g., 4.16 mm).

Figure 9:
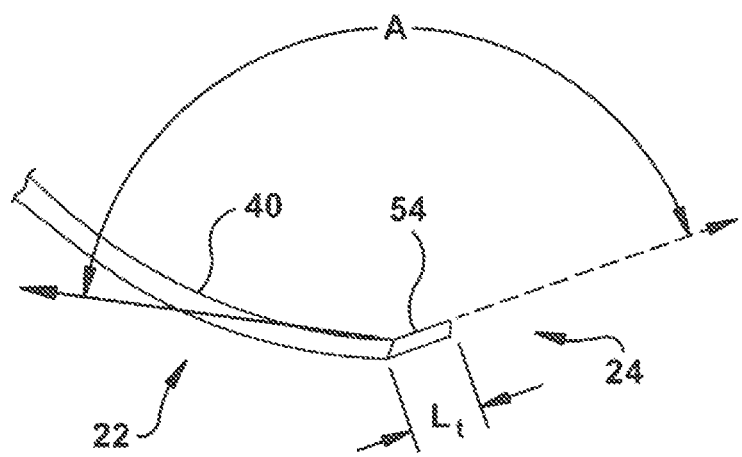
FIG. 9 is a magnified side view of the distal portion in FIG. 8.
Figure 10:
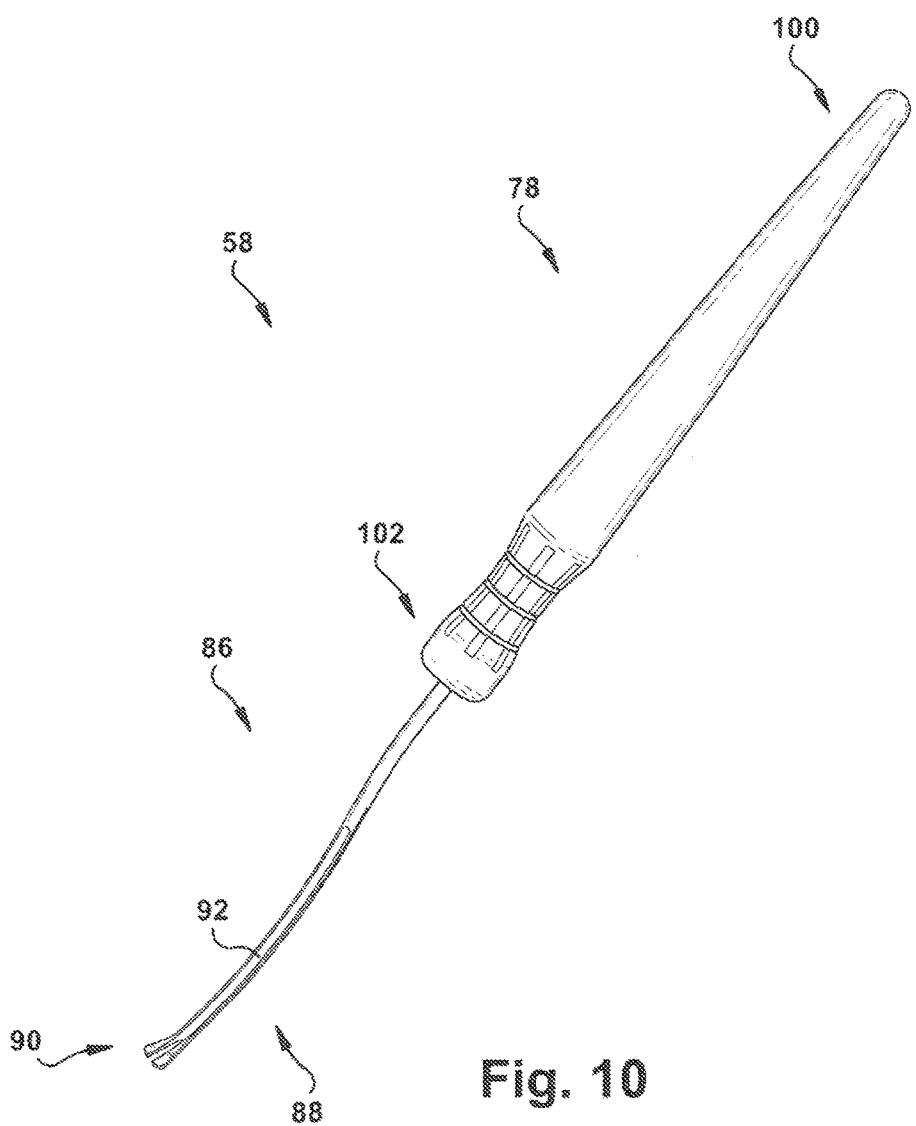
FIG. 10 is a perspective view of a surgical tool configured to deliver a neurostimulator to a craniofacial region of a subject constructed in accordance with another aspect of the present disclosure.

As shown in FIG. 9, the first surface 54 of the distal dissecting tip 24 extends at an offset angle A relative to the first major surface 40 of the distal portion 22. For example, all or only a portion of the distal dissecting tip 24 can have an increased curvature in the same plane as the distal portion curvature of the surgical tool 16. The offset angle A can be less than 180°. For example, the offset angle can be about 154°. This increased curvature at the distal dissecting tip 24 can allow greater contact with the posterior maxilla 12 as the surgical tool 16 is advanced toward the PPF 14.

The distal dissecting tip 24 also includes a leading edge 56, all or only a portion of which may be blunt or sharpened. For example, the leading edge 56 can have a rounded or curved cross-sectional profile similar to the leading dissection edge of known periosteal elevators. As shown in FIG. 8, the distal dissecting tip 24 can include a continuous leading edge 56. In this configuration, the continuous leading edge 56 forms a semi-circular, arc-shaped, or crescent shape without any interruptions. The degree to which the leading edge 56 is arched can be varied, for example, to impart the distal dissecting tip 24 with an oval-shaped configuration. As discussed above, the insertion groove 26 of the surgical tool 16 is tapered such that the second depth at the distal end 46 is less than the first depth at the proximal end 48 of the insertion groove. Consequently, when the distal dissecting tip 24 is advanced to the PPF 14, the distal dissecting tip must be elevated slightly from the tangent bony surface to allow the tunneling member 44 to be advanced into close proximity of the SPG 10.

Illustrated in FIG. 10 and FIGS. 13-17 is another aspect of the present disclosure comprising a surgical tool 58 configured to facilitate delivery a neurostimulator 60 (FIG. 11) to a craniofacial region of a subject. A neurostimulator 60 capable of being delivered by the surgical tool 58 can generally include any active implantable medical device configured to deliver electrical stimulation, alone or in combination with other types of stimulation to tissue of a subject. The neurostimulator 60 can further include any active implantable medical device configured for implantation for a relatively short period of time (e.g., to address acute medical conditions) or a relatively long period of time (e.g., to address chronic medical conditions). Additionally, the neurostimulator 60 can include one or more elements used to record or monitor a physiological response of a subject's tissue (e.g., a delivered therapy), as well as one or more other components that interface with the patient's tissue (e.g., therapeutic agent delivery mechanisms, sensors, etc.).

Figure 11:
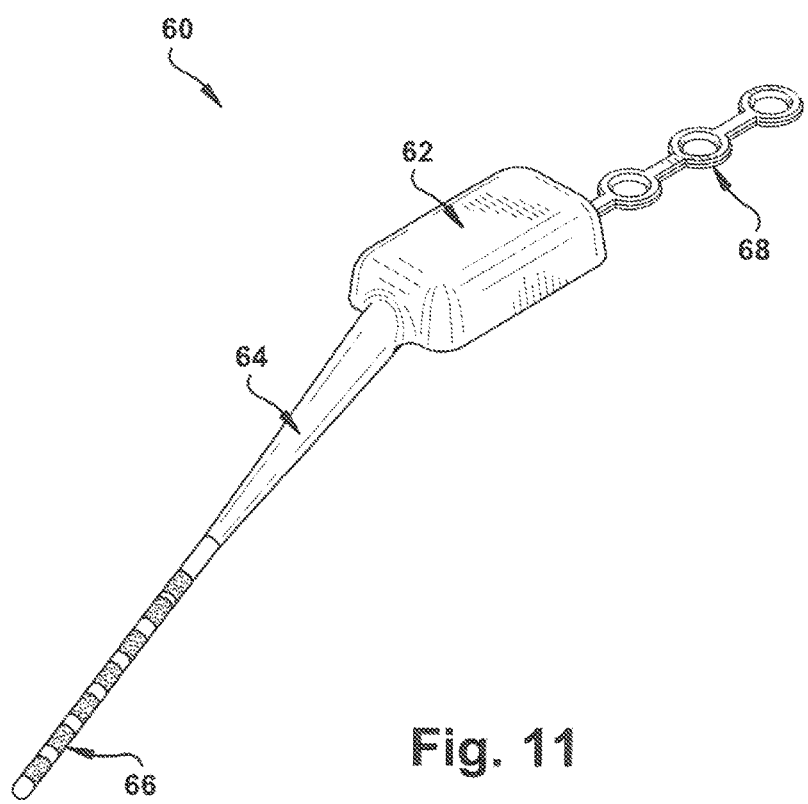
FIG. 11 is a perspective view of a neurostimulator that can be delivered to a craniofacial region of a subject using the surgical tool in FIG. 10.

In one example of the present disclosure, the neurostimulator 60 can be configured as shown in FIG. 11 and disclosed in U.S. patent application Ser. No. 12/765,712 (hereinafter, "the '712 application"), the entirety of which is hereby incorporated by reference. Briefly, the neurostimulator 60 can comprise a stimulator body 62, an integral stimulation lead 64, which includes one or more stimulating electrodes 66, and an integral fixation apparatus 68. The neurostimulator 60 can be implanted as disclosed in the '712 application, i.e., such that the stimulator body 62 is positioned sub-periosteally medial to the zygoma 70 on the posterior maxilla 12 within the buccal fat pad (not shown) of the cheek, and the integral fixation apparatus 68 is anchored to the zygomaticomaxillary buttress 72 such that the integral stimulation lead 64 is placed within the PPF 14 or, more specifically, in very close proximity to the SPG 10.

Figure 12:
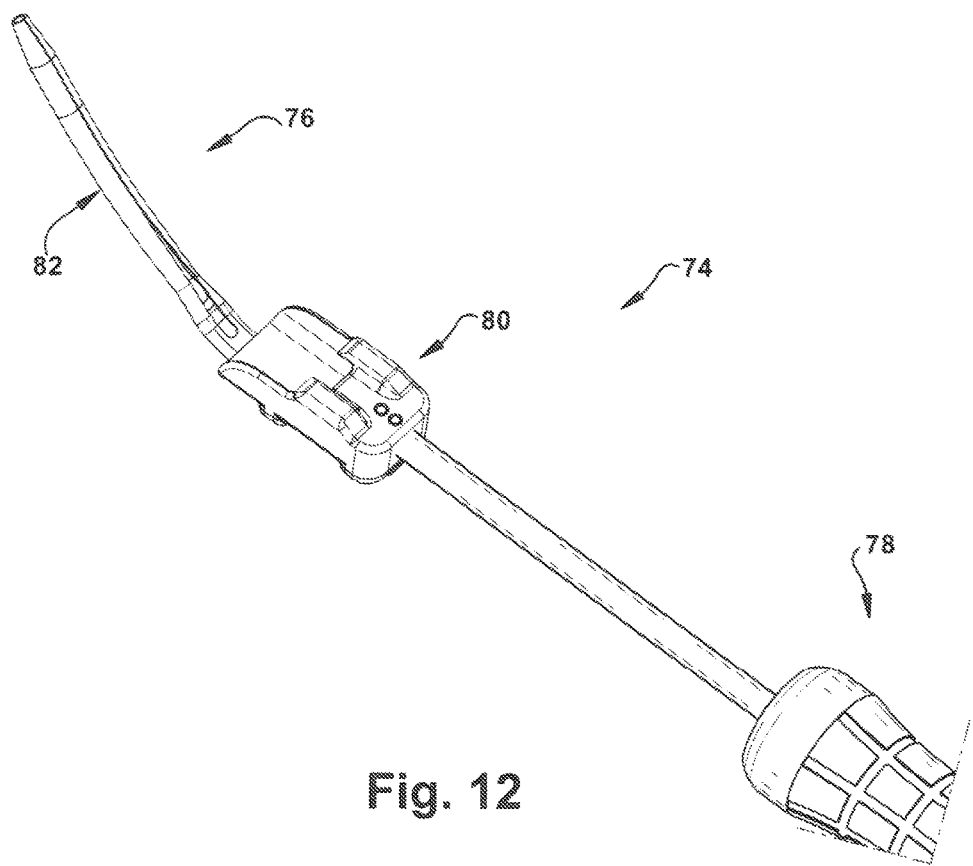
FIG. 12 is a schematic illustration showing a neurostimulator delivery apparatus.

As described in more detail below, the neurostimulator 60 can be deployed from the surgical tool 58 via a neurostimulator delivery apparatus 74 (FIG. 12). The neurostimulator delivery apparatus 74 includes an arcuate distal portion 76, a proximal handle portion 78, and an intermediate hub portion 80 that is integrally connected to each of the arcuate distal portion and the proximal handle portion. The intermediate hub portion 80 is configured and shaped to snugly receive a portion of the stimulator body 62. The arcuate distal portion 76 comprises a splittable sheath 82 that is securely affixed to a spine (not shown in detail).

Figure 13:
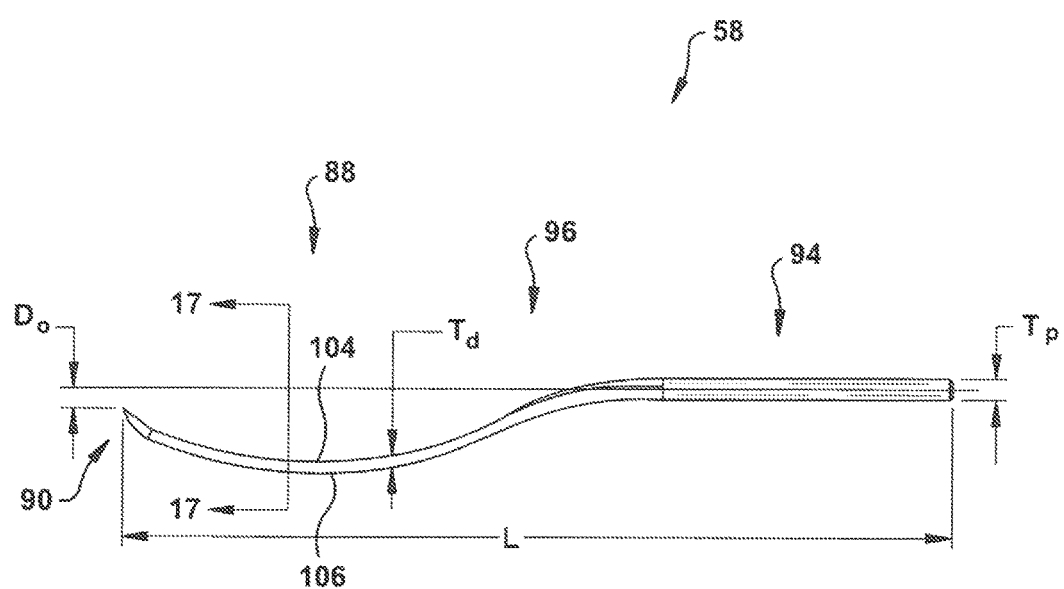
FIG. 13 is a side view of the surgical tool in FIG. 10 (handle omitted for clarity)

The surgical tool 58 (FIG. 10) of the present disclosure is designed and configured to facilitate delivery a neurostimulator 60 in very close proximity (e.g., about 1-5 mm) to the SPG 10 such that targeted electrical stimulation or delivery of electrical current from the neurostimulator to the SPG can be accomplished. As shown in FIG. 13, the surgical tool 58 comprises a handle portion 84, an elongate shaft 86 that includes a contoured distal portion 88 having a flared distal dissecting tip 90, and an insertion groove 92 on the elongate shaft. The surgical tool 58 is designed and configured to be inserted trans-orally from an incision located on the anterior maxilla 28.

The surgical tool 58 comprises a proximal portion 94, a contoured distal portion 88, and an intermediate portion 96 extending between the proximal portion and the distal portion. The proximal portion 94 and the intermediate portion 96 define a longitudinal plane P that extends between the proximal and intermediate portions. The surgical tool 58 can have a length L of about 10 cm to about 30 cm. For example, the surgical tool 58 can have a length L of about 12 cm (e.g., 12.4 cm). The surgical tool 58 can be made of a rigid or semi-rigid medical grade metal or metal alloy, such as titanium or stainless steel, medical grade plastics (e.g., PEEK, polycarbonate, nylon), ceramics (e.g., aluminum, zirconium oxide), combinations of metals, ceramics, plastics or plastic composites, and the like.

Figure 14:
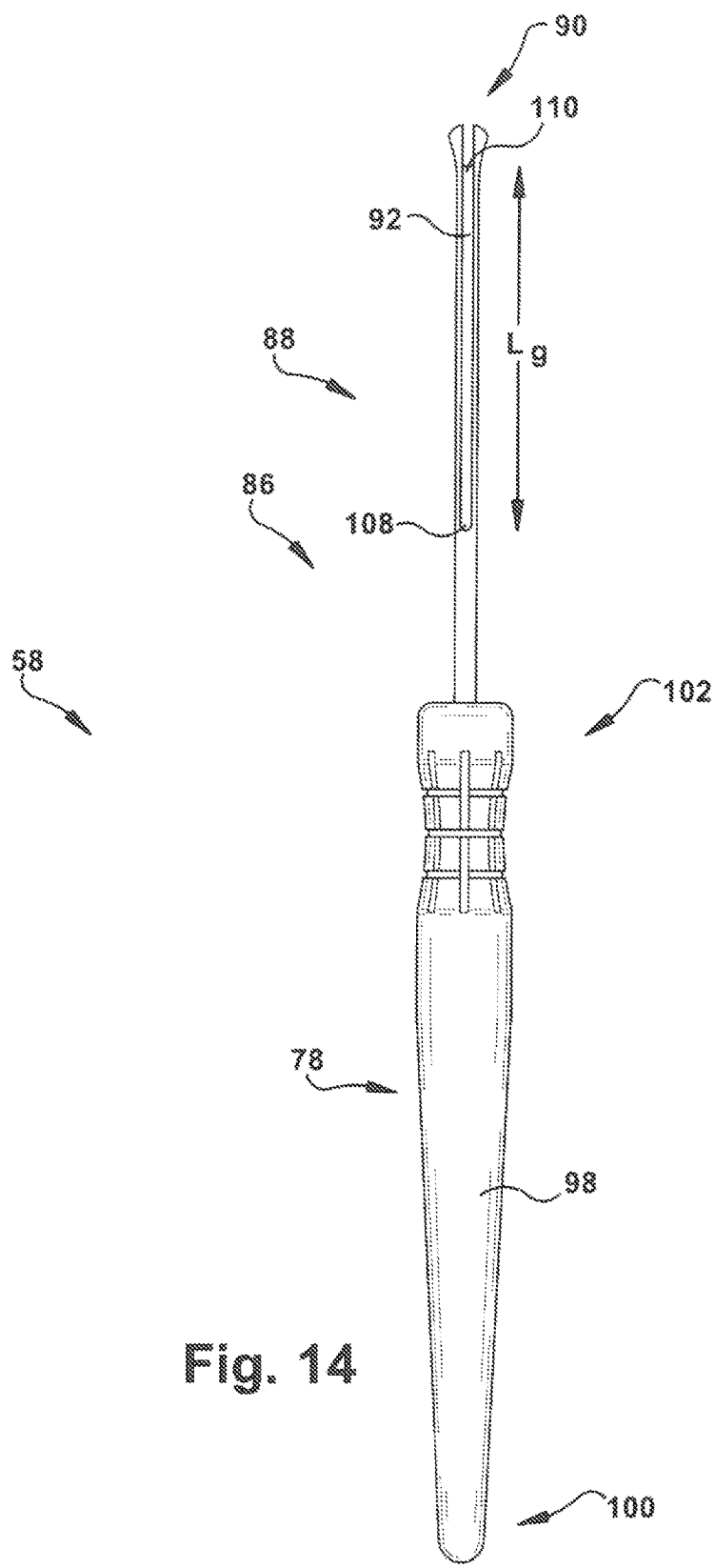
FIG. 14 is a top view of the surgical tool in FIG. 10.

The proximal portion 94 of the surgical tool 58 can have a thickness $T_p$ of about 2 mm to about 4 mm (e.g., about 3 mm). The intermediate portion 96 can have a thickness that is similar or identical to the thickness $T_p$ of the proximal portion 94. It will be appreciated, however, that the thickness of the intermediate portion 96 can decrease as the intermediate portion tapers to the distal portion 88. As shown in FIG. 14, the proximal portion 94 includes an ergonomic handle 98 that collectively forms the handle portion 84 and is securely disposed thereon. The handle 98 can have a length of about 6 cm to about 12 cm, and vary in diameter from a proximal end 100 (e.g., about 0.5 cm to about 3 cm) to a distal end 102 (e.g., about 0.5 cm to about 2 cm). The handle 98 can include various features to provide grip and tactile maneuverability, such as circumferential ridges or a cross-hatched precut pattern into the material forming the handle. The handle 98 can be made of a rigid or semi-rigid medical grade metal or metal alloy, such as stainless steel, medical grade plastics, polymers, and the like.

The distal portion 88 of the surgical tool 58 is shaped and configured to allow a user to simply and accurately traverse the anterior craniofacial skeletal anatomy to reach the PPF 14. The distal portion 88 is defined by oppositely disposed first and second major surfaces 104 and 106, which collectively form an arcuate shape relative to the longitudinal plane P. For example, the first major surface 104 of the distal portion 88 has a concave shape relative to the longitudinal plane P. The distal portion 88 can have a thickness $T_d$ of about 2 mm to about 5 mm. The thickness $T_d$ of the distal portion 88 can be uniform or, alternatively, the thickness $T_d$ can decrease or taper at the distal dissecting tip 90. The distal portion 88 can have a radius of curvature so that a user can maintain contact with the posterior maxilla 12 while advancing the surgical tool 58 to the PPF 14. For example, the distal portion 88 can have a radius of curvature of about 8 cm to about 3 cm.

To prevent unwanted rotation of the surgical tool 58 during use, the distal dissecting tip 90 can be offset from the longitudinal plane P. As shown in FIG. 13, the entire distal dissecting tip 90 can be offset a distance $D_o$ from the longitudinal plane P. The distance $D_o$ can be about 0.1 mm to about 5 mm. In one example of the present disclosure, the distance $D_o$ can be about 3 mm (e.g., 3 mm).

The surgical tool 58 (FIG. 14) additionally includes an insertion groove 92 on the elongate shaft 86 and, in particular, on the distal portion 88. The insertion groove 92 is adapted, shaped, and configured to facilitate precise, directional placement of a neurostimulator 60 within or about the PPF 14. For example, the insertion groove 92 can be shaped and configured to slidably receive, support, and guide the spine of the neurostimulator delivery apparatus 74. As shown in FIG. 14, the insertion groove 92 extends across the distal portion 88 of the surgical tool 58 between the distal dissecting tip 90 and the intermediate portion 96. For example, the insertion groove 92 can extend across only the distal portion 88 of the surgical tool 58 and not the intermediate portion 96 and/or the proximal portion 94.

Figure 17:
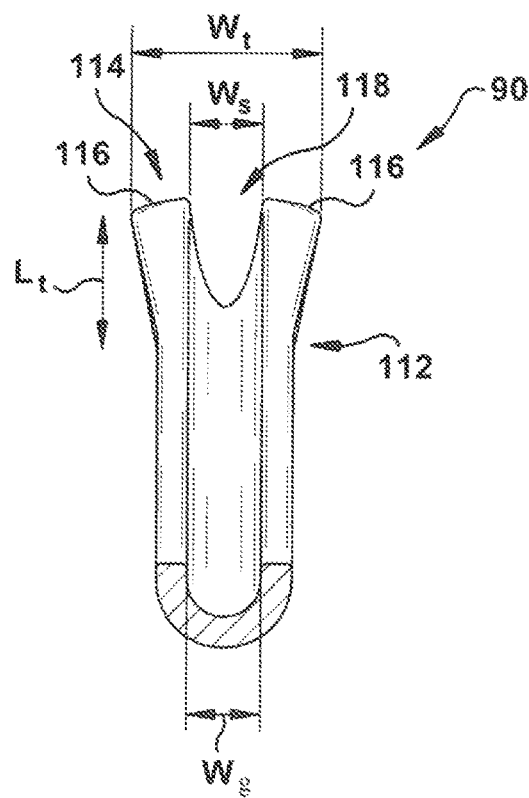
FIG. 17 is a cross-sectional view taken along Line 17-17 in FIG. 13.

The insertion groove 92 can be embedded or recessed in the first major surface 104 of the distal portion 88. The particular dimensions of the insertion groove 92 can vary depending upon the dimensions of surgical guide 58 and/or the dimensions of the neurostimulator delivery apparatus 74 (i.e., the spine). In one example of the present disclosure, the insertion groove 92 can have a depth of between about 0.5 mm and about 1.2 mm, a width $W_g$ (FIG. 11) of between about 1 mm and about 2 mm (e.g., 1.6 mm), and a length $L_g$ (FIG. 6B) of between about 2 cm and about 8 cm (e.g., 6 cm). Although the insertion groove 92 is shown in FIG. 17 as having a semi-circular cross-sectional shape, it will be appreciated that the insertion groove can have other cross-sectional shapes (e.g., square-shaped, V-shaped, etc.) to facilitate engagement of the surgical tool 58 with the neurostimulator delivery apparatus 74.

Figure 15:
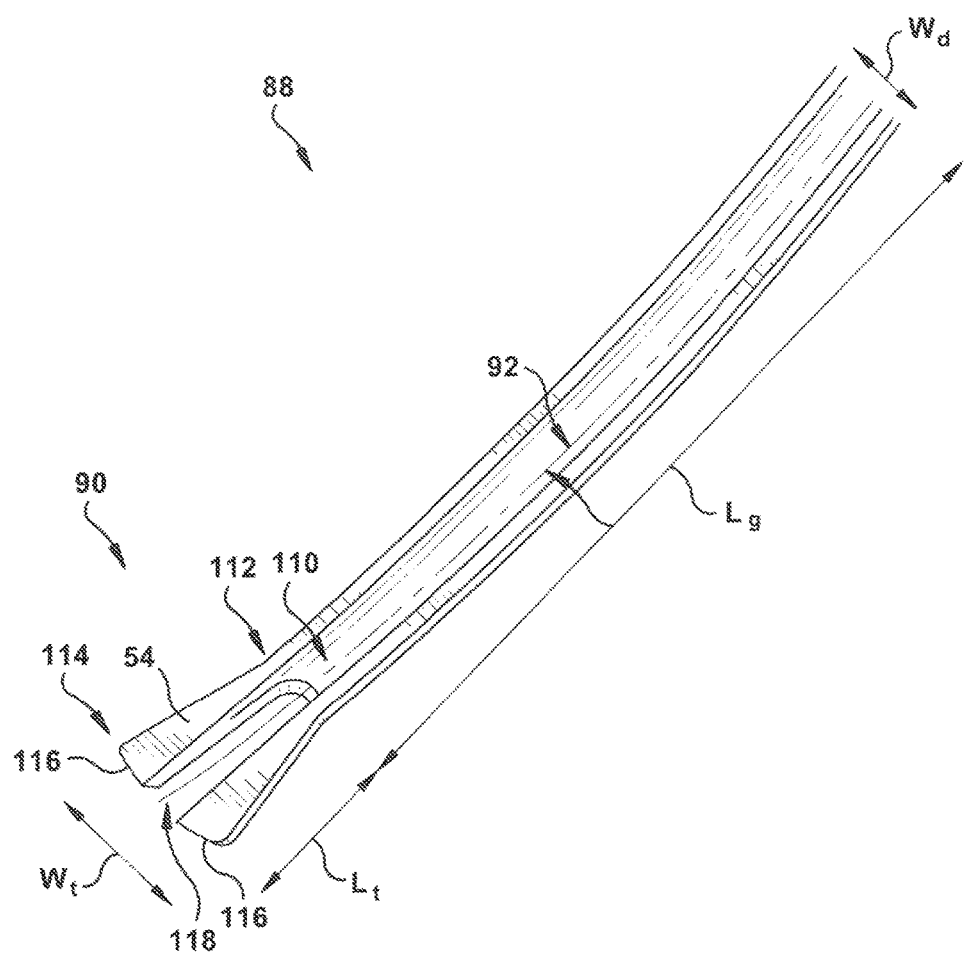
FIG. 15 is a magnified perspective view showing the distal portion of the surgical tool in FIG. 14.

Referring to FIG. 15, the depth and width $W_g$ of the insertion groove 92 can remain uniform across the length $L_g$ of the insertion groove to facilitate engagement and release of the neurostimulator delivery apparatus 74 to and from the surgical tool 58. For example, the insertion groove 92 can have a depth that is the same or substantially the same across the length $L_g$ of the insertion groove. That is, the proximal end 108 of the insertion groove 92 can include a first depth that is equal to or about equal to a second depth at the distal end 110 of the insertion groove. Alternatively, the depth and width $W_g$ of the insertion groove 92 can vary across the length $L_g$ of the insertion groove. For example, the depth of the insertion groove 92 can taper from the distal end 110 of the insertion groove to the proximal end 108 of the insertion groove, where the insertion groove is no longer present as it reaches the discharge slot 118. In another example, the depth of the insertion groove 92 at the proximal end 108 can gradually decrease towards the distal end 110 of the distal dissecting tip 90 until the insertion groove meets the discharge slot 118 and is thus no longer present.

The distal portion 88 of the surgical tool 58 can include a flared distal dissecting tip 90. By "flared" it is meant that all or only a portion of the distal dissecting tip 90 is shaped and configured to extend away from the distal portion 88 of the elongated shaft 86 axially and/or distally, and typically also radially. The distal dissecting tip 90 includes a length $L_t$ that extends between a proximal end 112 and a distal end 114 thereof. The length $L_t$ can be about 0.1 cm to about 1 cm, such as about 0.5 cm (e.g., 0.25 cm). The distal dissecting tip 90 also includes a width $W_t$ that increases from the proximal end 112 to the distal end 114 of the tip. The width $W_t$ of the distal dissecting tip 90 is greater than the width $W_d$ of the distal portion 88. In one example of the present disclosure, the width $W_t$ at the distal end 114 of the distal dissecting tip 90 can be about 2.5 mm to about 6 mm (e.g., 4.16 mm).

As described above with reference to FIG. 9, a first surface 54 of the distal dissecting tip 24 and 90 extends at an offset angle A relative to the first major surface 40 and 104 of the distal portion 22 and 88 (respectively). For example, all or only a portion of the distal dissecting tip 90 can have an increased curvature in the same plane as the distal portion curvature of the surgical tool 58. The offset angle A can be less than 180°. For example, the offset angle can be about 154°. This increased curvature at the distal dissecting tip 90 can allow greater contact with the posterior maxilla 12 as the surgical tool 58 is advanced toward the PPF 14. In addition, the offset angle A may be configured or dimensioned to add thickness to the surgical tool 58 and thereby prevent the sharp leading edge 56 from entering the PPF 14 and damaging the SPG 10 or other soft tissue structure(s) (e.g., other nerves, blood vessels, etc.).

Figure 16:
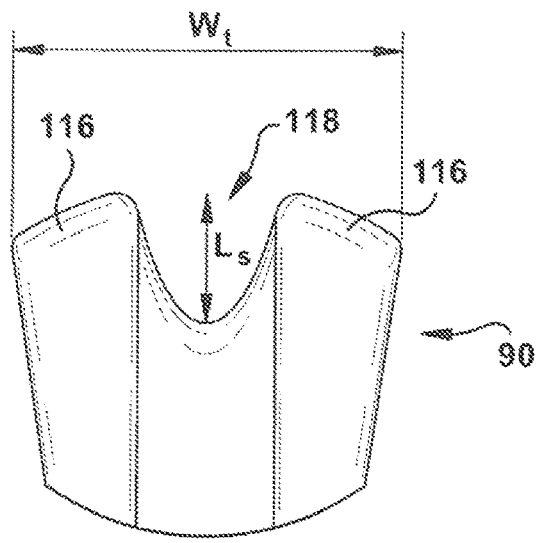
FIG. 16 is a magnified perspective view showing a distal dissecting tip of the surgical tool in FIG. 10.

The distal dissecting tip 90 also includes a leading edge 116, all or only a portion of which may be blunt or sharpened. As shown in FIGS. 16-17, the distal dissecting tip 90 has a bifurcated configuration such that the leading edge 116 is interrupted and a discharge slot 118 is formed within the distal dissecting tip. When the distal dissecting tip 90 is inserted into or about the PPF 14 (e.g., at the opening of the PPF), the discharge slot 118 allows the stimulation lead 64 of the neurostimulator 60 to be inserted into the PPF without removing or elevating the distal dissecting tip from the tangent bony surface.

The discharge slot 118 includes a width $W_s$ and a length $L_s$. The width $W_s$ of the discharge slot 118 can be less than the width $W_t$ of the distal dissecting tip 90. In one example of the present disclosure, the width $W_s$ of the discharge slot 118 can equal, or be about equal to, the width $W_g$ of the insertion groove 92, which can be configured and dimensioned to accept the stimulation lead 64 of the neurostimulator 60. The length $L_s$ of the discharge slot 118 can be less than the length $L_t$ of the distal dissecting tip 90 (FIGS. 16-17) or, alternatively, the length $L_s$ of the discharge slot can be about equal to the length $L_t$ of the distal dissecting tip (FIG. 15). Additionally, the length $L_t$ of the distal dissecting tip 90 in FIGS. 14-15 can be less than the length $L_t$ of the distal dissecting tip in FIGS. 16-17. The discharge slot 118 can have an elongated, U-shaped configuration (FIG. 15), a V-shaped configuration (FIGS. 16-17), or any other desired configuration.

Figure 18:
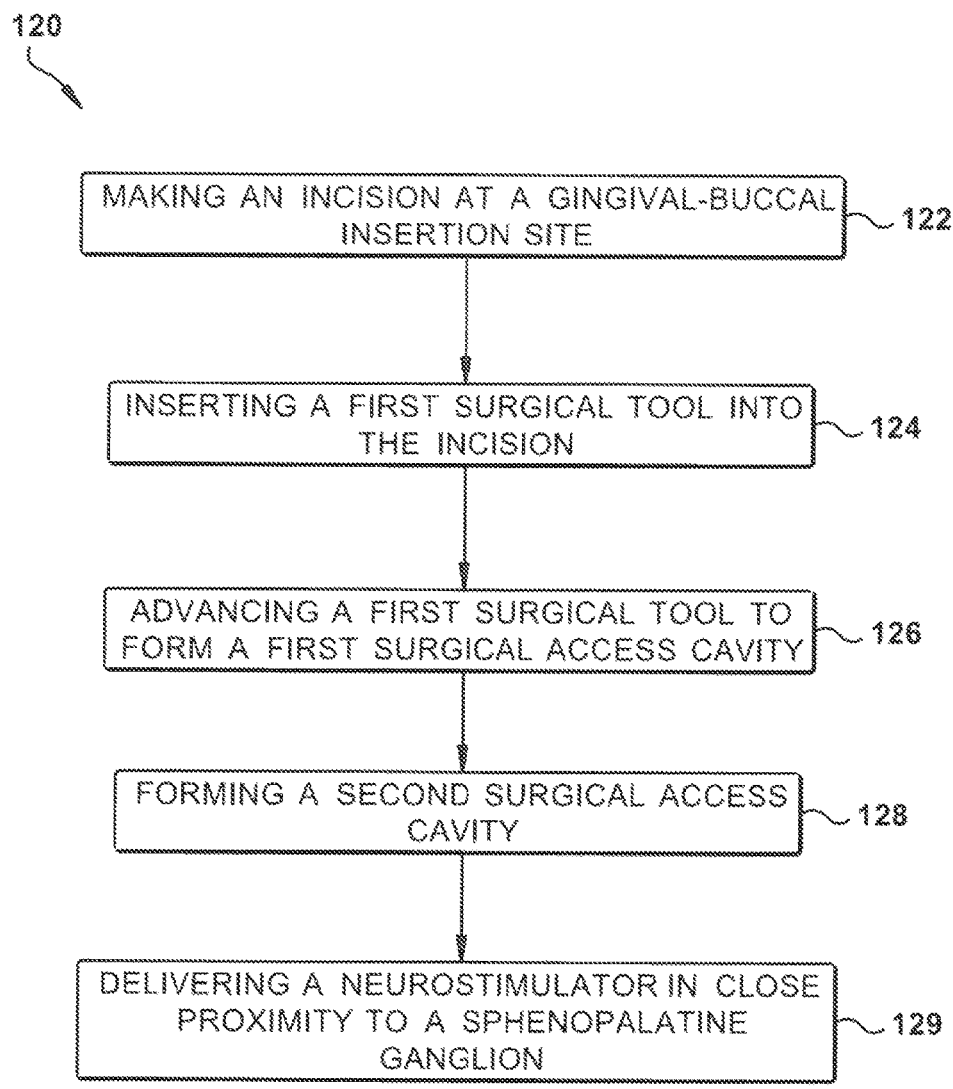
FIG. 18 is a process flow diagram illustrating a method for delivering a neurostimulator to within close proximity of a sphenopalatine ganglion (SPG) according to another aspect of the present disclosure.
Figure 19:
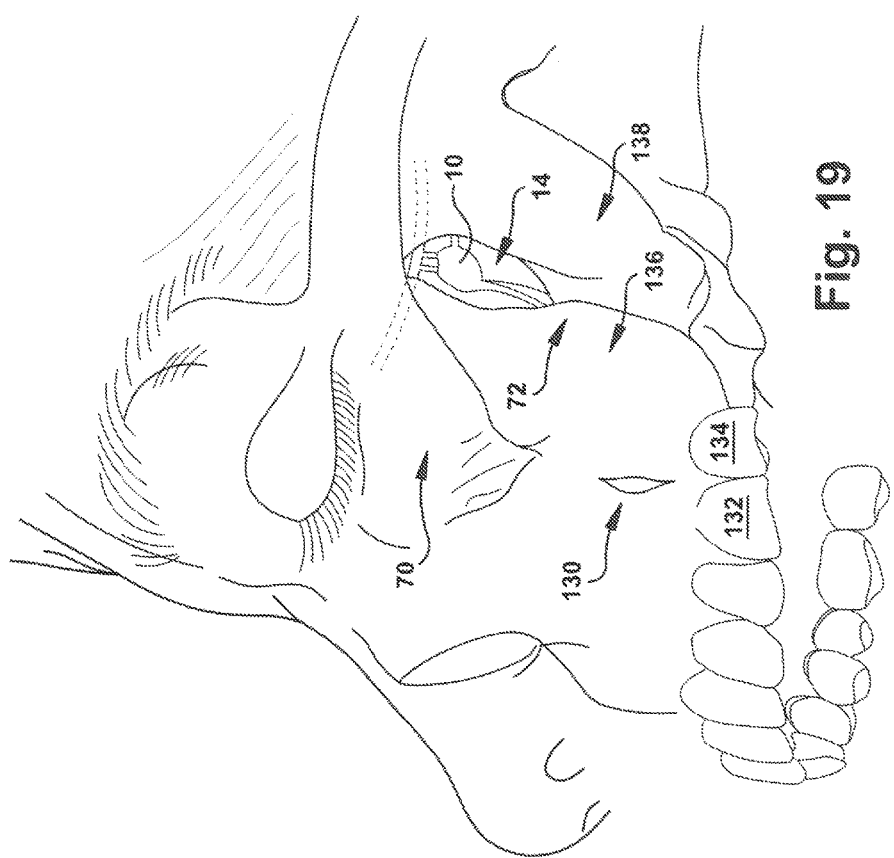
FIG. 19 is a perspective view of the anterior craniofacial skeleton showing a gingival-buccal insertion site.

Illustrated in FIG. 18 is another aspect of the present disclosure including a method 120 for delivering a neurostimulator 60 to within close proximity of a SPG 10. At Step 122 of the method 120, an incision 130 (FIG. 19) is made at a gingival-buccal insertion site. The incision 130 can be made in a similar or identical manner as disclosed in U.S. Patent Publication No. 2010/0185258 A1 to Papay, which is hereby incorporated by reference in its entirety. Briefly, for example, a #10 scalpel blade (not shown) can be used to make an incision 130 in a superior-inferior manner between the second and third molars 132 and 134.

Figure 20:
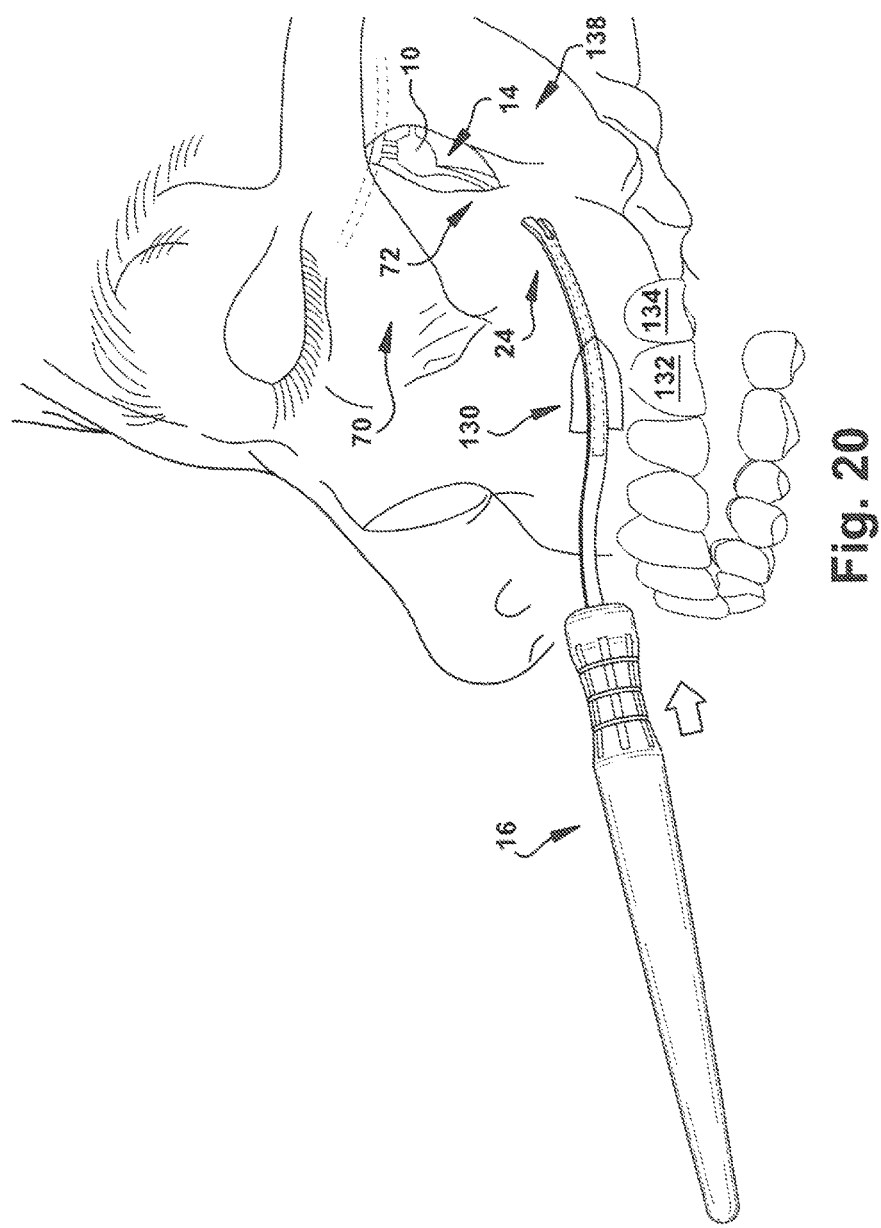
FIG. 20 is a perspective view showing the surgical tool of FIGS. 2A-B being inserted into the gingival-buccal insertion site.

At Step 124, the surgical tool 16 shown in FIGS. 2A-B (referred to below as "the first surgical tool") in then inserted into the incision 130 as shown in FIG. 20. Prior to inserting the first surgical tool 16, however, the surgical anatomy of the subject is determined using one or more imaging techniques (e.g., MRI, CT, ultrasound, X-ray, fluoroscopy, or combinations thereof). In particular, the anatomy of the subject's skull, including the location and size of the PPF 14 can be determined prior to insertion of the first surgical tool 16.

After inserting the first surgical tool 16 into the incision 130, the first surgical tool is urged in a posterior direction so that the first major surface 40 of the distal portion 22 traverses under the zygomatic bone 70 along the maxillary tuberosity 136. The first surgical tool 16 is then advanced further until the distal dissecting tip 24 engages the junction formed by the posterior maxillary buttress 72 and the pterygoid plate 138, just inferior and lateral to the PPF 14. Advancement of the first surgical tool 16 may naturally stop when the distal dissecting tip 24 is correctly positioned at the junction formed by the posterior maxillary buttress 72 and the pterygoid plate 138.

Figure 21:
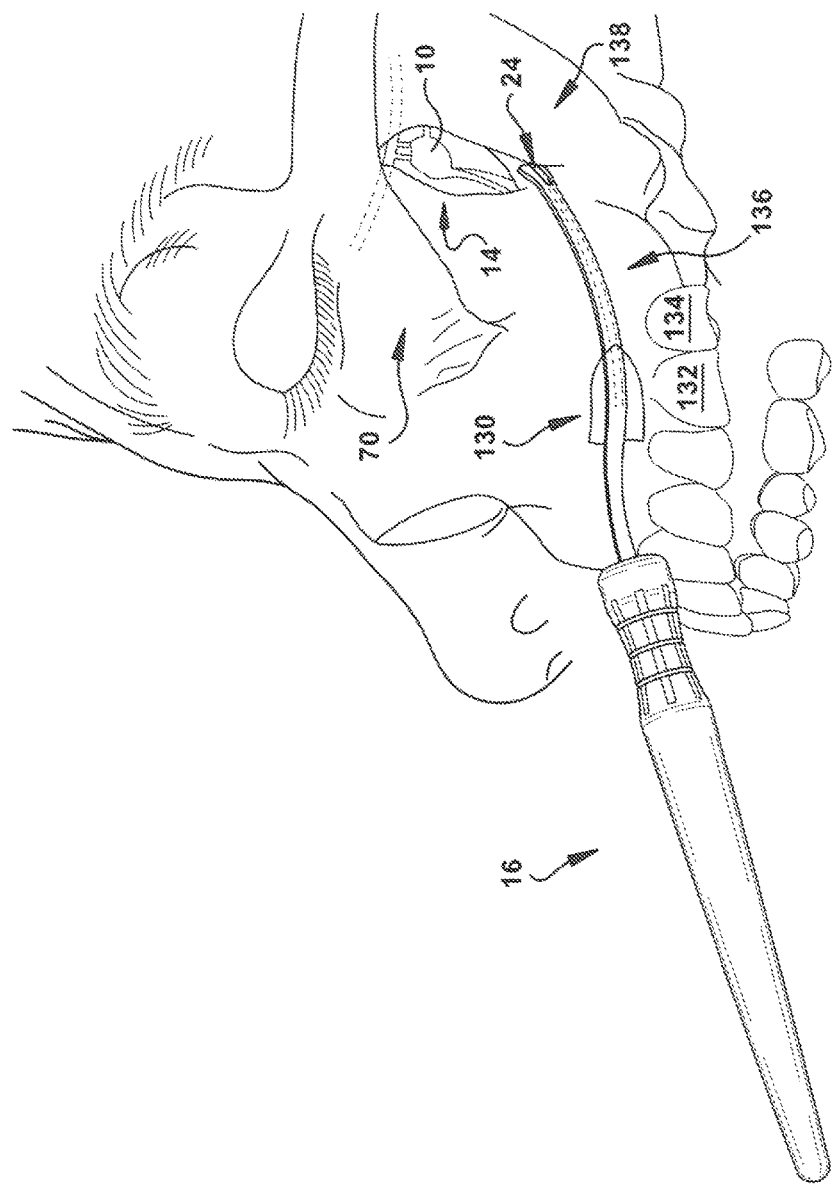
FIG. 21 is a perspective view showing the distal dissecting tip of the surgical tool in FIG. 20 engaging the junction formed by the posterior maxillary buttress and the pterygoid plate.

At this point, the first surgical tool 16 is rotated in a superior direction until the distal dissecting tip 24 is within (or nearly within) the PPF 14 (FIG. 21). This can be done by carefully "walking" the distal dissecting tip 24 up the pterygoid plate 138 until the distal dissecting tip (or other desired portion of the distal portion 22) slides into the PPF 14. At Step 126, advancement and positioning of the first surgical tool 16 from the incision to the PPF 14 forms a surgical access cavity 140 (FIG. 22). As can be more clearly seen in FIG. 22, the surgical access cavity 140 is shaped like a tunnel or trough that extends from an open end 142 of the incision 130 to the PPF 14. The first surgical tool 16 can then be removed to expose the surgical access cavity 140.

Figure 23:
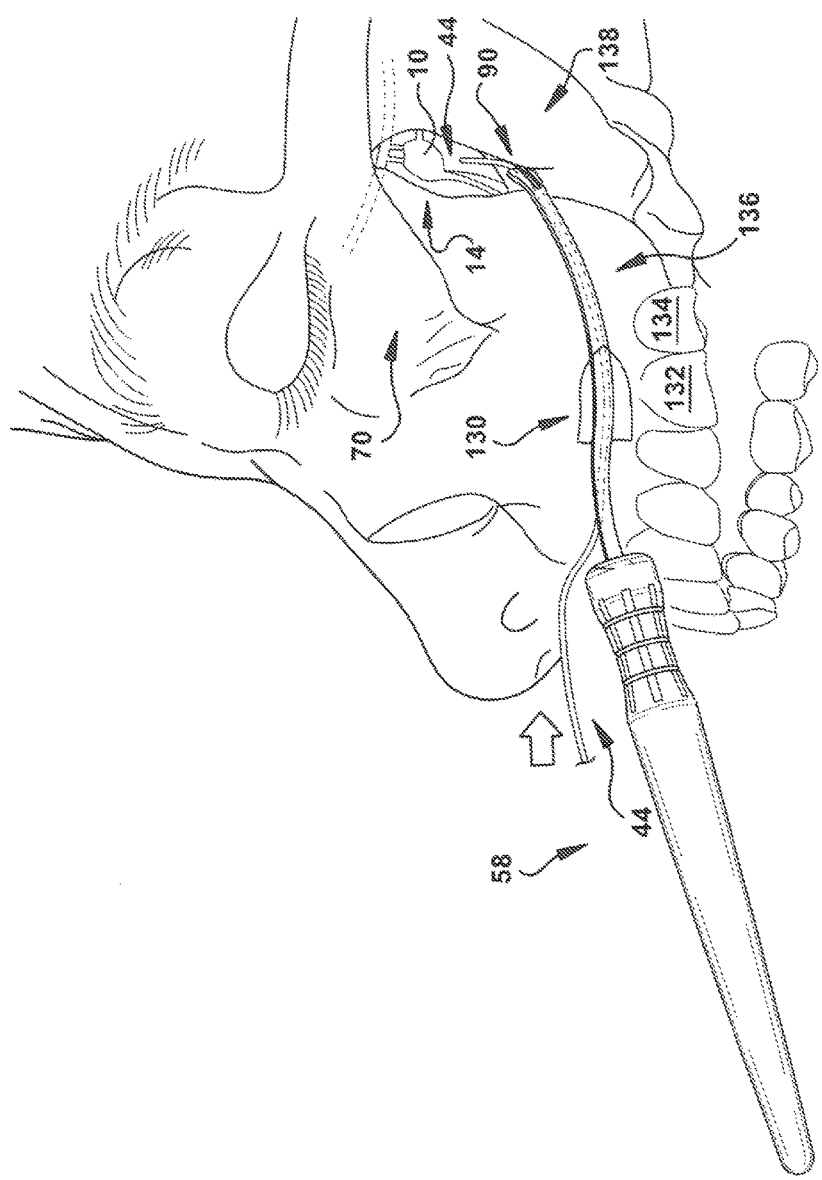
FIG. 23 is a perspective view showing a tunneling member being mated with an insertion groove of the surgical tool in FIG. 14.

Next, the surgical tool 58 (referenced to below as "the second surgical tool") is inserted into the surgical access cavity 140 as shown in FIG. 23. After the second surgical tool 58 is appropriately positioned in the surgical access cavity 140, an electrode lead blank 44 is carefully inserted into the insertion groove 92 of the second surgical tool 58 and then progressively advanced along the insertion groove. The electrode lead blank 44 can be configured to have the same or substantially the same dimensions as the stimulation lead 64 of the neurostimulator 60. Although not shown in detail, the electrode lead blank 44 can comprise an elongated, flexible wire-like structure having a distal end configured to bluntly dissect tissue. The electrode lead blank 44 is urged along the insertion groove 92 until the distal end of the electrode lead blank extends from the surgical access cavity 140 into close proximity with the SPG 10.

It will be appreciated that the second surgical tool 58 can be configured with the distal dissecting tip 90 shown in FIGS. 14-15 or FIGS. 16-17 depending, for example, on the craniofacial anatomy of the subject. For example, it may be preferable to use a second surgical tool 58 configured with the distal dissecting tip 90 shown in FIGS. 14-15 in instances where the PPF 14 of a subject having a pterygomaxillary fissure with a large width (e.g., greater than 3 mm). In such instances, the longer distal dissecting tip 90 shown in FIGS. 14-15 (as compared to the distal dissecting tip in FIGS. 16-17) permits easier access to the posterior portion of the PPF 14. In other instances, it may be preferable to use the distal dissecting tip 90 shown in FIGS. 16-17 for narrower anatomic fissures, e.g., less than 3 mm due to the shorter tip length (as compared to the distal dissecting tip in FIGS. 14-15).

Figure 24:
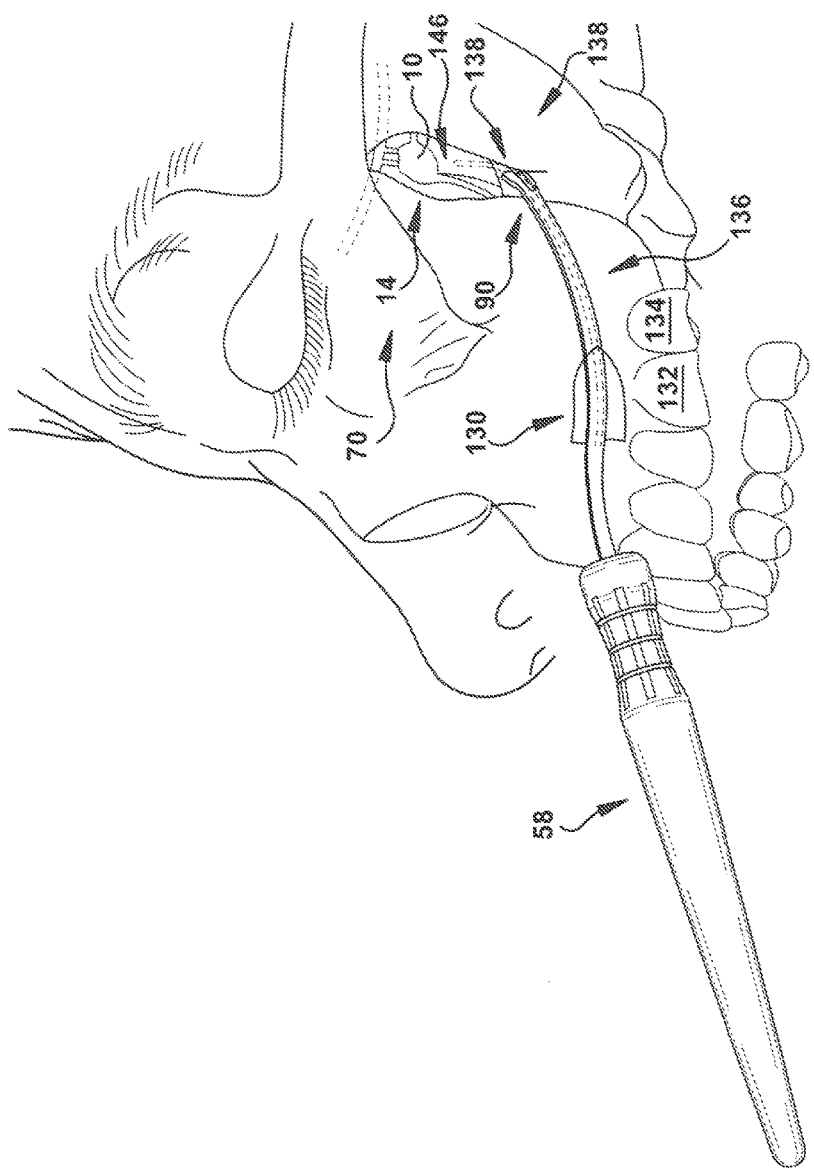
FIG. 24 is a perspective view showing the surgical tool in FIG. 23 following withdrawal of the tunneling member.
Figure 25:
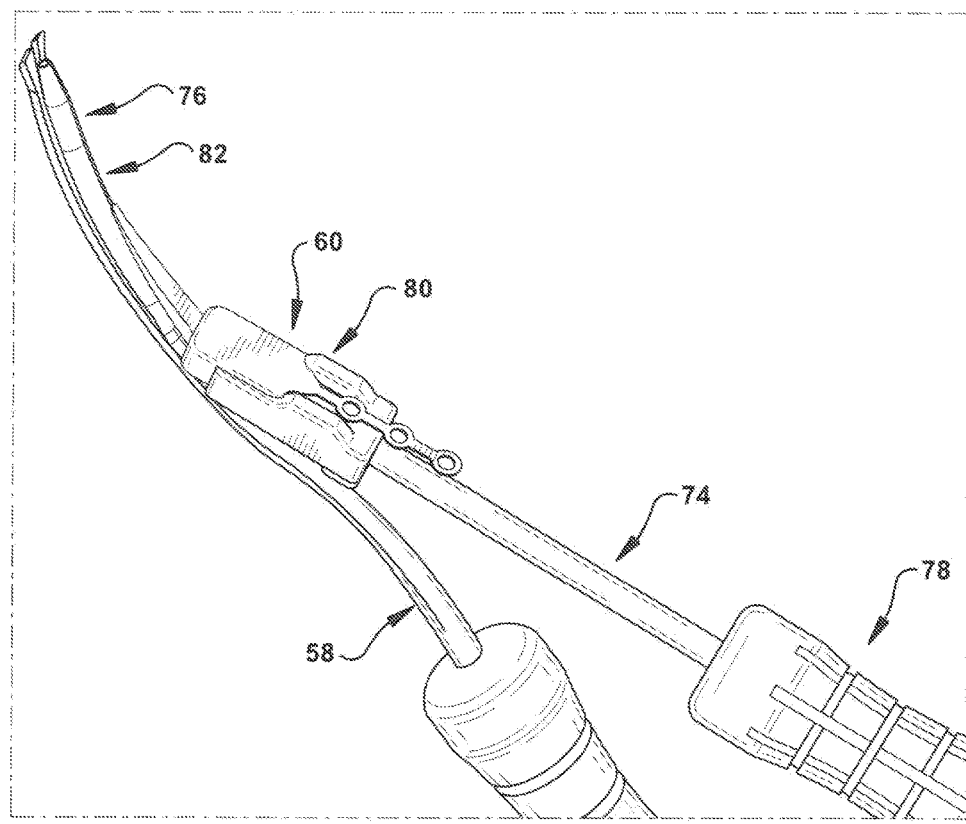
FIG. 25 is a schematic illustration showing a neurostimulator delivery apparatus being used to load a neurostimulator (FIG. 11) onto the surgical tool in FIG. 24.

As shown in FIG. 24, the electrode lead blank 44 is then removed from the subject. Next, the neurostimulator deployment apparatus 74 is mated with the second surgical tool 58 (FIG. 25). For example, the spine of the neurostimulator deployment apparatus 74 can slidably engage the insertion groove 92 of the second surgical tool 58. Once the neurostimulator deployment device 74 is properly mated with the second surgical tool 58, the neurostimulator 60 is deployed from the neurostimulator deployment apparatus (Step 129). The neurostimulator 60 can then be implanted within the subject as discussed above and disclosed in the '712 application. With the neurostimulator 60 securely implanted within the subject, an electrical current from the neurostimulator can be applied to the SPG 10 to treat a medical condition (e.g., headache). Advantageously, use of the electrode lead blank 44 with the second surgical tool 58 provides a pathway to the PFF 14 (and thus the SPG 10) that can be accurately followed by the stimulation lead 64 as there is no need to remove or adjust the position of the second surgical tool prior to implantation of the neurostimulator 60.

From the above description of the invention, those skilled in the art will perceive improvements, changes and modifications. Such improvements, changes, and modifications are within the skill of the art and are intended to be covered by the appended claims.

Having described the invention, the following is claimed:

1. A method for delivering a neurostimulator to within close proximity of a sphenopalatine ganglion (SPG), said method comprising the steps of:
   making an incision at a gingival-buccal insertion site;
   inserting a first surgical tool into the incision;
   advancing the first surgical tool under a zygomatic bone along a maxillary tuberosity towards a PPF to form a first surgical access cavity;
   forming a second surgical access cavity at an end of the first surgical access cavity that is in close proximity to the SPG; and
   delivering the neurostimulator in close proximity to the SPG via the first and second surgical access cavities.

2. The method of claim 1, wherein said advancing step further comprises the steps of:
   advancing the first surgical tool until a distal dissecting tip of the first surgical tool engages a junction formed by a posterior maxillary buttress and a pterygoid plate; and
   rotating the first surgical tool in a superior direction until the distal dissecting tip is positioned about the PPF.

3. The method of claim 1, wherein said step of forming a second surgical access cavity further comprises the steps of:
   advancing a tunneling member into contact with an insertion groove of the first surgical tool;
   urging the tunneling member along the insertion groove into contact with an end of the first surgical access cavity; and
   advancing the tunneling member through the end of the first surgical access cavity to form the second surgical access cavity.

4. The method of claim 1, wherein said step of delivering the neurostimulator includes the further steps of:
   withdrawing the first surgical tool and the tunneling member from the first and second surgical access cavities, respectively;
   securely mating the neurostimulator with a neurostimulator delivery device, the neurostimulator including a stimulation lead and the neurostimulator delivery device including a spine;
   advancing a second surgical tool into the first surgical access cavity;
   slidably engaging the spine with an insertion groove of the second surgical tool until the stimulation lead is positioned within the second surgical access cavity;
   disengaging the neurostimulator from the neurostimulator deployment apparatus; and
   securing the neurostimulator about the PPF so that the stimulation lead is in close proximity to the SPG.

5. The method of claim 1, wherein the neurostimulator is programmed to deliver an electrical current to the SPG to treat a medical condition.

6. The method of claim 5, wherein the medical condition is pain.

7. The method of claim 6, wherein the pain is at least one of headache and facial pain.

8. A method comprising the steps of:
   receiving a first surgical tool through an incision at a gingival-buccal insertion site of a subject;
   receiving the first surgical tool under a zygomatic bone along a maxillary tuberosity towards a pterygopalatine fossa (PPF) to form a first surgical access cavity;
   receiving a tunneling member at an end of the first surgical access cavity to form a second surgical access cavity that is in close proximity to the sphenopalatine ganglion (SPG); and
   receiving a neurostimulator in close proximity to the SPG via the first and second surgical access cavities.

9. The method of claim 8, further comprising the step of applying, by the subject, an electrical current from the neurostimulator to the SPG to treat a medical condition.

10. The method of claim 9, wherein the medical condition is pain.

11. The method of claim 10, wherein the pain is at least one of headache and facial pain.

* * * * *